(12) United States Patent
Lietzau et al.

(10) Patent No.: US 8,609,714 B2
(45) Date of Patent: Dec. 17, 2013

(54) THIOPHENE COMPOUNDS FOR LIQUID-CRYSTALLINE MEDIA

(75) Inventors: Lars Lietzau, Darmstadt (DE); Louise Diane Farrand, Dorset (GB); Markus Czanta, Darmstadt (DE); Harald Hirschmann, Darmstadt (DE); Michael Wittek, Erzhausen (DE); Izumi Saito, Darmstadt (DE); Brigitte Schuler, Grossostheim (DE)

(73) Assignee: MERCK PATENT GmbH, Darmstadt (DE)

( * ) Notice: Subject to any disclaimer, the term of this patent is extended or adjusted under 35 U.S.C. 154(b) by 173 days.

(21) Appl. No.: 13/202,153

(22) PCT Filed: Feb. 16, 2010

(86) PCT No.: PCT/EP2010/000968
§ 371 (c)(1),
(2), (4) Date: Aug. 18, 2011

(87) PCT Pub. No.: WO2010/094455
PCT Pub. Date: Aug. 26, 2010

(65) Prior Publication Data
US 2011/0301360 A1    Dec. 8, 2011

(30) Foreign Application Priority Data

Feb. 19, 2009  (DE) .......................... 10 2009 009 630
Sep. 7, 2009  (DE) .......................... 10 2009 040 215

(51) Int. Cl.
*A61K 31/381*  (2006.01)
*C07D 333/28*  (2006.01)

(52) U.S. Cl.
USPC .......................................... 514/445; 549/61

(58) Field of Classification Search
USPC .......................................... 514/445; 549/61
See application file for complete search history.

(56) References Cited

U.S. PATENT DOCUMENTS

| 5,728,319 A | 3/1998 | Matsui et al. |
| 5,792,386 A | 8/1998 | Matsui et al. |
| 5,858,270 A | 1/1999 | Matsui et al. |

FOREIGN PATENT DOCUMENTS

| EP | 0 467 260 A2 | 1/1992 |
| EP | 0 786 445 A1 | 7/1997 |
| JP | 2007-84487 A | 4/2007 |
| WO | WO 2009/129915 A1 | 10/2009 |
| WO | WO 2010/099853 A1 | 9/2010 |

OTHER PUBLICATIONS

King, Med. Chem. Principle and Practice (1994), pp. 206-208.*
International Search Report of PCT/EP2010/000968 (Jun. 14, 2010).

* cited by examiner

*Primary Examiner* — Taofiq A Solola
(74) *Attorney, Agent, or Firm* — Millen, White, Zelano & Branigan, P.C.

(57) ABSTRACT

The invention relates to liquid-crystalline compounds of the formula I

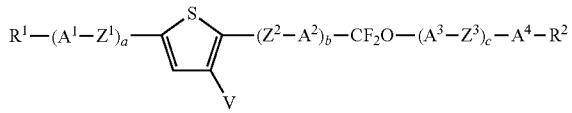

in which $R^1$, $R^2$, $A^1$, $A^2$, $A^3$, $A^4$, $Z^1$, $Z^2$, $Z^3$, V, a, b and c have the meanings indicated in Claim 1, and to liquid-crystalline media comprising at least one compound of the formula I, and to electro-optical displays containing a liquid-crystalline medium of this type.

23 Claims, No Drawings

THIOPHENE COMPOUNDS FOR LIQUID-CRYSTALLINE MEDIA

The invention relates to thiophene derivatives containing a difluoromethyleneoxy group and to the use thereof as component(s) in liquid-crystalline media (LC media). In addition, the present invention relates to liquid-crystal and electro-optical display elements which contain the liquid-crystalline media according to the invention.

In recent years, the areas of application of liquid-crystalline compounds have broadened considerably to display devices, electro-optical equipment, electronic components, sensors, etc., of various types. For this reason, a number of different structures have been proposed, in particular in the area of nematic liquid crystals. The nematic liquid-crystal mixtures have to date found the broadest use in flat display devices. They have been employed, in particular, in passive TN or STN matrix displays or systems having an active TFT matrix.

The compounds according to the invention can be used as component(s) of liquid-crystalline media (LC media), in particular for displays based on the principle of the twisted cell, the guest-host effect, the effect of deformation of aligned phases DAP or ECB (electrically controlled birefringence), the IPS (in-plane switching) effect or the effect of dynamic scattering.

Various compounds containing a difluoromethyleneoxy bridge as liquid-crystalline material and the preparation thereof have been described, such as, for example, in the specification EP 0786445 A1.

Thiophene derivatives have occasionally been investigated as liquid-crystalline substances. EP 0467260 A2 discloses compounds containing a 2,5-thiophenediyl unit. However, the compounds are predominantly smectic. Modern display applications use mostly nematic liquid-crystal media.

The present invention was based on the object of finding novel stable compounds which are suitable as component(s) of liquid-crystalline media. In particular, the compounds should simultaneously have comparatively low viscosity and a dielectric anisotropy in the positive region. For many modern mixture concepts in the area of liquid crystals, it is advantageous to use compounds having high dielectric anisotropy $\Delta\epsilon$.

In view of the very wide variety of areas of application of such compounds having a high $\Delta\epsilon$, it was desirable to have available further compounds, preferably having high nematogeneity, which have properties precisely customised to the particular applications.

One object of the invention was thus to find novel stable compounds which are suitable as component(s) of liquid-crystalline media, in particular for, for example, TN, STN, IPS and TN-TFT displays.

A further object of the present invention was to provide compounds which, alone or in mixtures, have high dielectric anisotropy $\Delta\epsilon$ and a high clearing point. In addition, the compounds according to the invention should be thermally and photochemically stable under the conditions prevailing in the areas of application. Furthermore, the compounds according to the invention should have the broadest possible nematic phase. As mesogens, they should facilitate a broad nematic phase in mixtures with liquid-crystalline co-components and be extremely readily miscible with nematic base mixtures, in particular at low temperatures.

Surprisingly, it has been found that the thiophene derivatives according to the invention are eminently suitable as components of liquid-crystalline media. They can be used, in particular, to obtain liquid-crystalline media which are suitable for TN-TFT or IPS displays. The compounds according to the invention are stable, even on exposure to air, and colourless. They are also distinguished by particularly strongly positive dielectric anisotropies $\Delta\epsilon$, owing to which lower threshold voltages are necessary on use in optical switching elements. They have a broad nematic phase range alone or in mixtures. In addition, the compounds according to the invention have a particularly low melting point, a high clearing point, and at the same time low values for the rotational viscosity $\gamma_1$. Compared with substances from the prior art which have a similar property profile, a particularly low melting point is observed, in particular, in the case of the compounds containing three ring systems. The substances thus have a much lower tendency towards crystallisation than corresponding conventional compounds. The compounds according to the invention can therefore be employed, for example, in higher concentration.

The provision of the thiophene derivatives according to the invention very generally considerably broadens the range of liquid-crystalline substances which are suitable, from various applicational points of view, for the preparation of liquid-crystalline mixtures.

The invention thus relates to compounds of the formula I

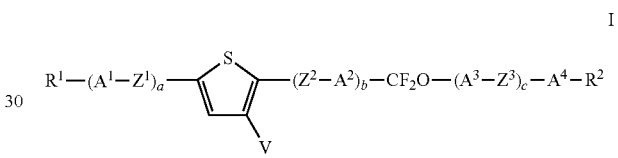

in which $R^1$ and $R^2$ each, independently of one another, denote H, a halogenated or unsubstituted alkyl radical having 1 to 15 C atoms, where, in addition, one or more $CH_2$ groups in these radicals may each be replaced, independently of one another, by —C≡C—, —CH=CH—, —(CO)O—, —O(CO)—, —(CO)— or —O— in such a way that O atoms are not linked directly to one another, where $R^2$ additionally and preferably denotes F, Cl, Br, CN, SCN, NCS or $SF_5$, $A^1$, $A^2$, $A^3$ and $A^4$ each, independently of one another, identically or differently, denote:

a) trans-1,4-cyclohexylene or cyclohexenylene, in which, in addition, one or two non-adjacent $CH_2$ groups may be replaced by —O— and/or —S—, and in which H may be replaced by F, b) 1,4-phenylene, in which one or two CH groups may be replaced by N, and in which, in addition, one or more H atoms may be replaced by Br, Cl, F, CN, methyl, methoxy or a mono- or polyfluorinated methyl or methoxy group, or c) a radical from the group 1,4-bicyclo[2.2.2]octylene, piperidine-1,4-diyl, cyclobut-1,3-diyl, spiro[3.3]heptane-2,6-diyl,

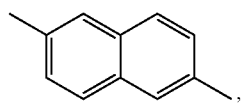
,

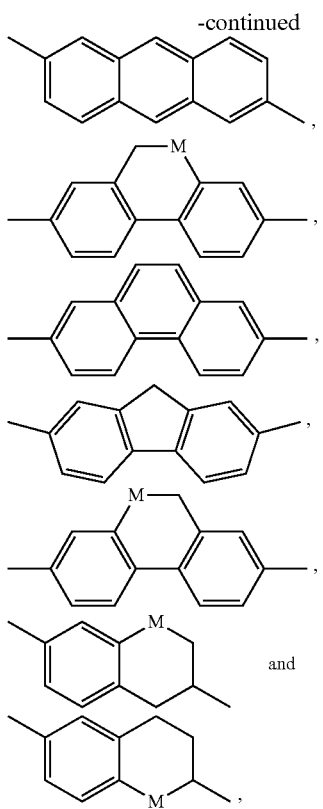

in which one or more hydrogen atoms may be replaced by F, CN, SON, SF$_5$, CH$_2$F, CHF$_2$, CF$_3$, OCH$_2$F, OCHF$_2$ or OCF$_3$, one or more double bonds may be replaced by single bonds, one or more CH groups may be replaced by N, M denotes —O—, —S—, —CH$_2$—, —CHY— or —CYY$^1$—, and Y and Y$^1$ denote Cl, F, CN, OCF$_3$ or CF$_3$, V denotes H, F or Cl, preferably H or F, Z$^1$, Z$^2$ and Z$^3$ each, independently of one another, identically or differently, denote a single bond, —CH$_2$O—, —(CO)O—, —CF$_2$O—, —CH$_2$CH$_2$CF$_2$O—, —CF$_2$CF$_2$—, —CH$_2$CF$_2$—, —CH$_2$CH$_2$—, —(CH$_2$)$_4$—, —CH=CH—, —CH=CF—, —CF=CF— or —C≡C—, where asymmetrical bridges may be oriented to both sides, a denotes 0, 1 or 2, preferably 0 or 1, particularly preferably 0,
b denotes 0, 1, 2 or 3, preferably 1 or 2, and
c denotes 0, 1 or 2, preferably 0,
where a+b+c≤4, is preferably equal to 1, 2 or 3, particularly preferably 1 or 2.

A$^{1-3}$ and Z$^{1-3}$ may independently also adopt different meanings if they occur more than once for a, b or c>1.

The invention furthermore relates to the use of the compounds of the formula I in liquid-crystalline media.

The present invention likewise relates to liquid-crystalline media comprising at least two liquid-crystalline components which comprise at least one thiophene derivative of the formula I.

The compounds of the formula I have a broad range of applications. Depending on the choice of substituents, these compounds can serve as base materials of which liquid-crystalline media are predominantly composed; however, compounds of the formula I can also be added to liquid-crystalline base materials from other classes of compound in order, for example, to modify the dielectric and/or optical anisotropy of a dielectric of this type and/or in order to optimise its threshold voltage and/or its viscosity.

In the pure state, the compounds of the formula I are colourless and, alone or in mixtures, form liquid-crystalline mesophases in a temperature range which is favourably located for electro-optical use. The compounds according to the invention can be used to achieve broad nematic phase ranges. In liquid-crystalline mixtures, the compounds according to the invention increase the clearing point and significantly increase the polarity of the mixture.

Z$^1$ and/or Z$^3$ preferably denote a single bond, —CF$_2$O—, —OCF$_2$—, —C$_2$F$_4$—, —CH$_2$O—, —OCH$_2$— or —(CO)O—, in particular a single bond. Z$^2$ preferably denotes —CH$_2$CH$_2$—, —CH=CH—, —C≡C— or a single bond, in particular a single bond.

In the case where Z$^2$ is a single bond, A$^2$ preferably denotes an unsaturated or aromatic ring from groups b) or c) in accordance with the definition of the formula I.

If present, A$^1$, A$^2$, A$^3$ and A$^4$ preferably denote

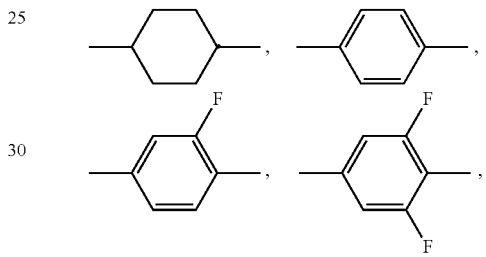

and furthermore

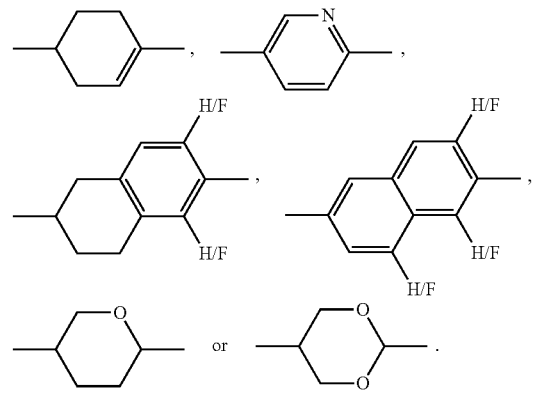

If present, the group A$^1$ preferably denotes

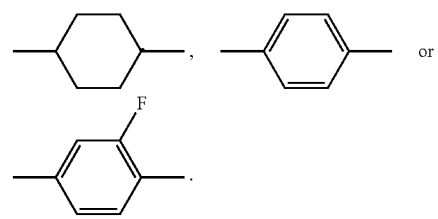

If present, $A^2$ preferably denotes

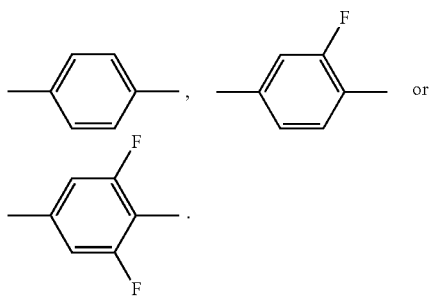

If present, $A^4$ preferably denotes

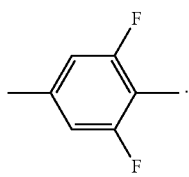

in particular

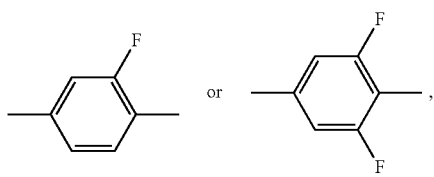

$R^1$ preferably denotes alkyl, alkoxy, alkenyl or alkenyloxy having up to 8 carbon atoms. $R^1$ particularly preferably denotes straight-chain alkyl or alkenyl.

$R^2$ preferably denotes a polar radical X, where

X denotes F, Cl, $OCF_3$, $OCHF_2$, $OCHFCF_3$, $OCF_2CHFCF_3$, $CF_3$, CN, $SF_5$, NCS, NCO, SCN, OCN, in particular F, Cl, CN, $CF_3$ or $OCF_3$ and very particularly F or $OCF_3$.

$R^1$ and $R^2$ preferably do not simultaneously denote H.

Particular preference is given to compounds of the formula IA

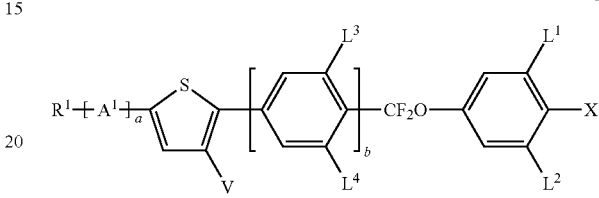

IA in which $R^1$, $A^1$, X, a, b and V have the meanings indicated above for formula I, and $L^1$, $L^2$, $L^3$ and $L^4$ denote H or F.

Preference is given to compounds of the formula IA in which $L^1$ denotes fluorine. b preferably denotes 1 or 2, in particular 1. V is preferably H. $L^3$ is preferably F. a+b is preferably 1 or 2. b is very particularly preferably 1, and a is preferably 0. It is particularly preferred for 2, 3 or 4 of the groups $L^1$ to $L^4$ to be fluorine.

In a further embodiment of the invention, preference is given to compounds of the formula I in which V denotes F. The compounds have particularly high dielectric anisotropy.

Particularly preferred compounds of the formula I are the compounds of the formulae I1 to I6:

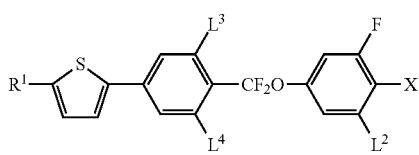

I1

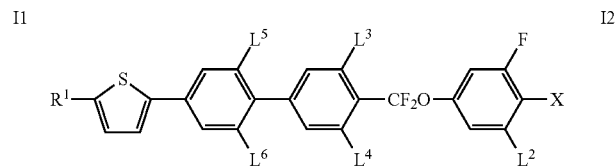

I2

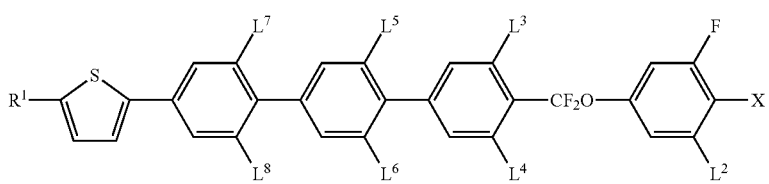

I3

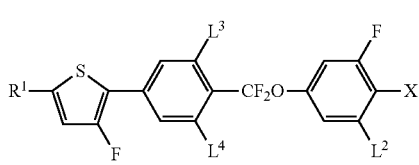

I4

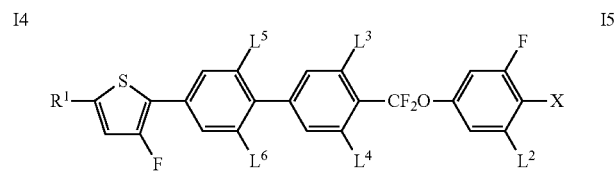

I5

-continued
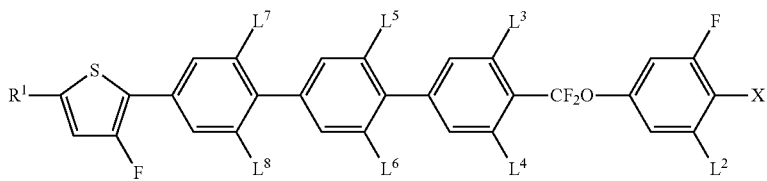
in which R¹ and X have the meanings indicated above. L², L³, L⁴, L⁵, L⁶, L⁷ and L⁸ denote, independently of one another, H or F.
L², L³ and L⁴ particularly preferably denote, independently of one another, a radical F.
L⁵ and L⁷ preferably denote, independently of one another, H.
Examples of particularly preferred compounds are the following:
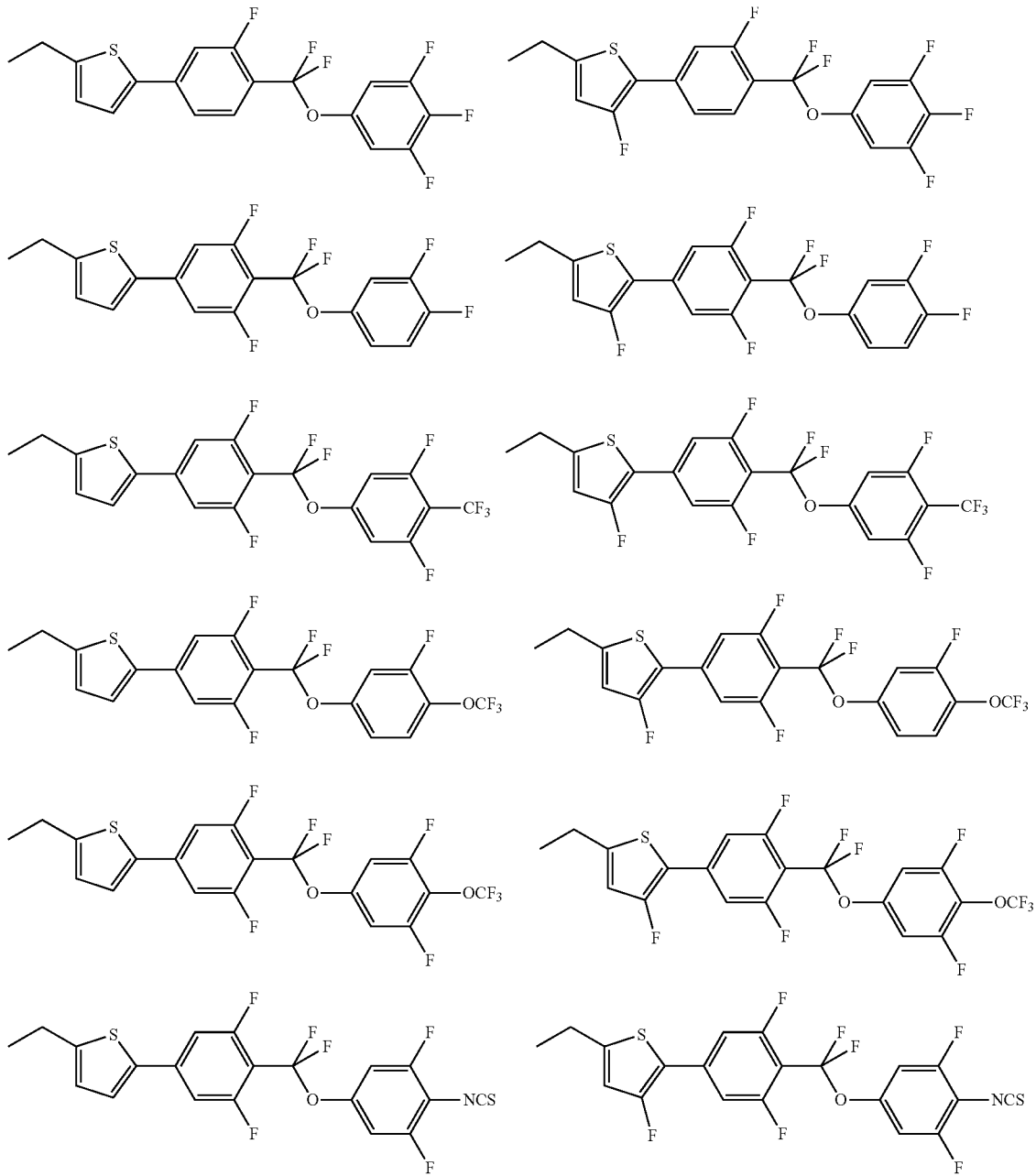

-continued
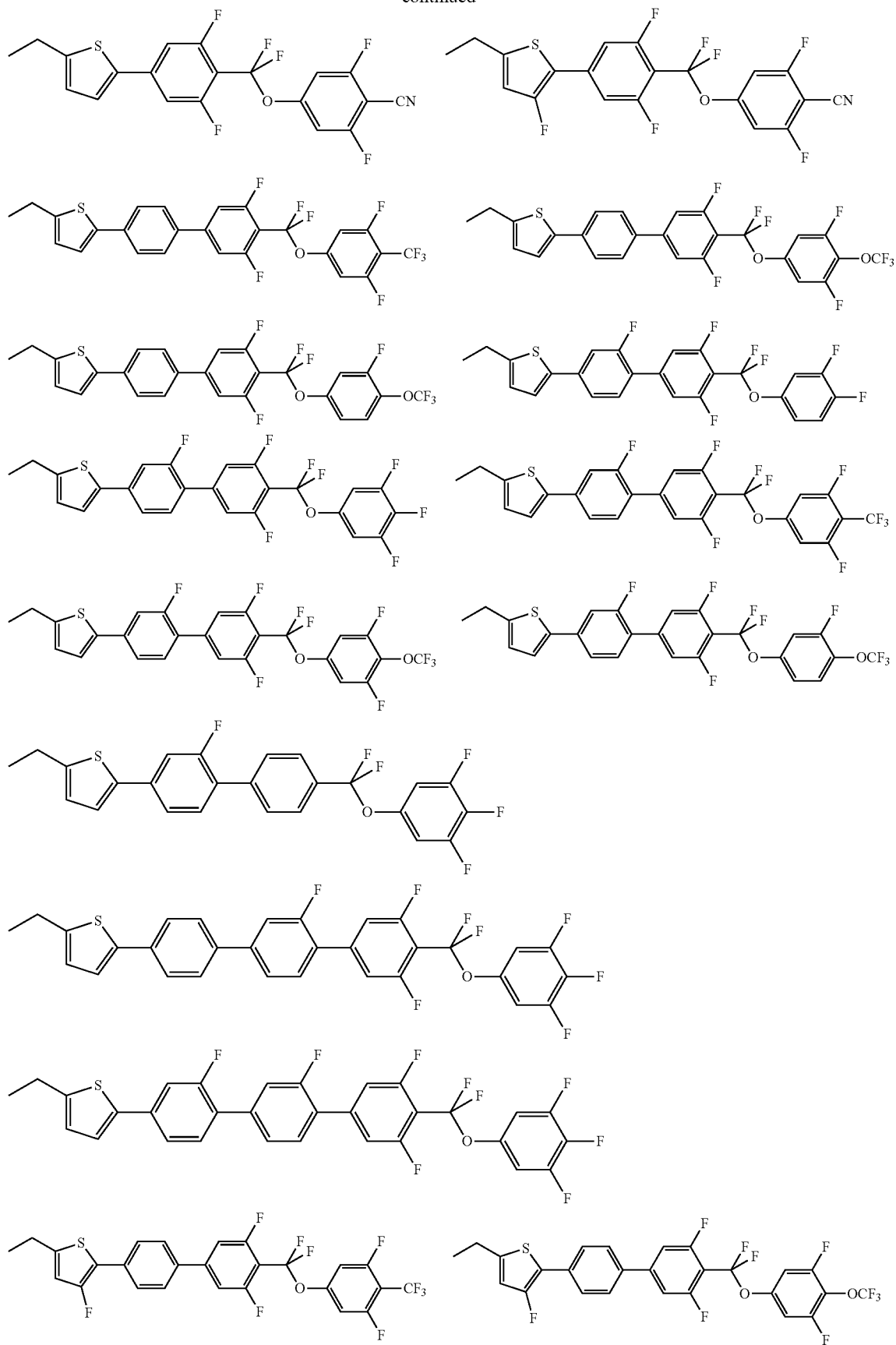

-continued

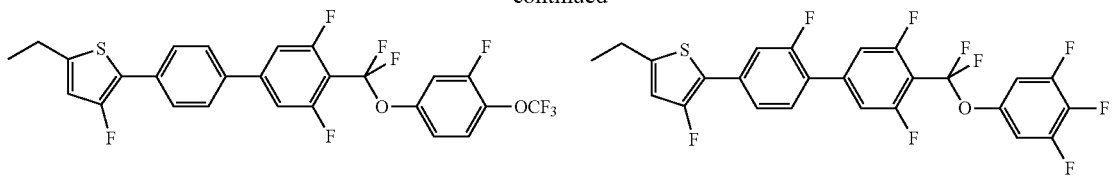

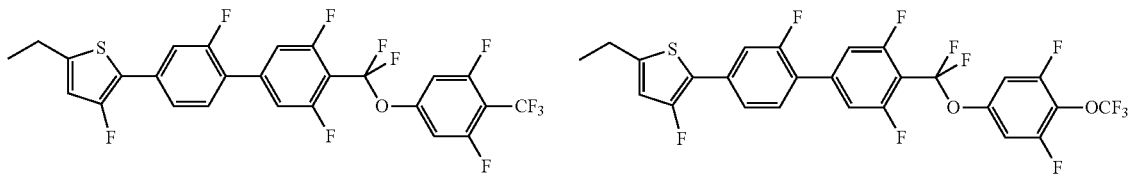

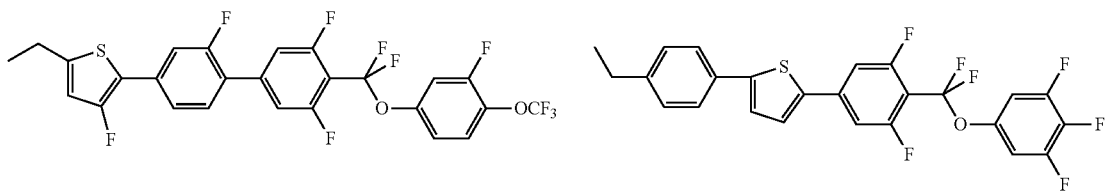

In the case of compounds which can occur in the form of diastereomers, both the pure substances and also any mixing ratio of the isomers are encompassed and are in each case to be regarded as suitable mixture component.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compounds of the formula I can advantageously be prepared as can be seen from the following illustrative syntheses (Schemes 1 and 2):

Scheme 1.
Variant of the synthesis of the thiophene derivatives of the formula I.

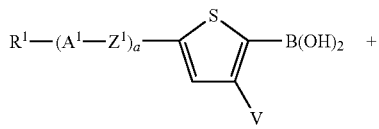

The synthesis in accordance with Scheme 1 is based on a Suzuki coupling.

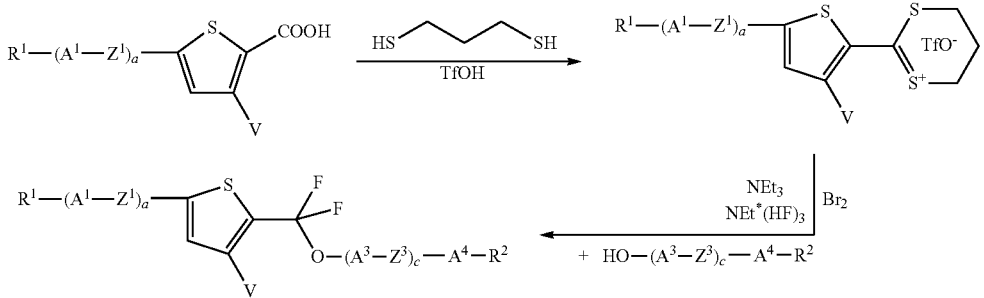

The synthesis in Scheme 2 is based on a known synthesis of the —CF$_2$O— group as indicated, for example, in the specification EP 1341742 A1.

The groups in the formulae in Schemes 1 and 2 which do not participate can be varied so long as it is suggested by the definitions of the compounds of the formula I. Corresponding starting materials can generally readily be prepared by the person skilled in the art. Thus, the compounds of the formulae I and IA can be prepared.

The invention therefore also relates to a process for the preparation of compounds of the formula I:

A process for the preparation of compounds of the formula I in which V denotes hydrogen or fluorine is characterised in that it comprises a process step in which a 2-substituted thiophene of the formula IIa or IIb

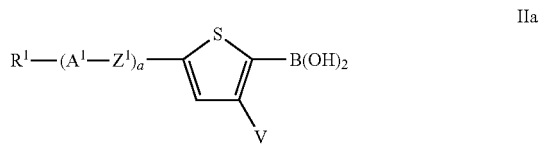

IIa or a corresponding boronate containing the end group —B(OH)$_3^-$ or —B(OH)$_3$M, in which M denotes a monovalent ionic radical as counterion to the boronate (in particular an alkali metal ion, such as Na$^+$, K$^+$, etc.), or

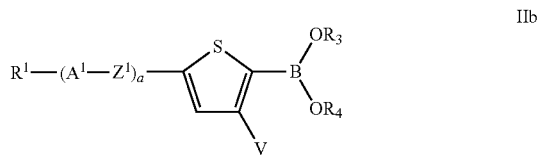

IIb in which R$^1$, A$^1$, Z$^1$, V and a are as defined in claim 1, and
R$^3$, R$^4$ denote alkyl having 1-12 C atoms or R$^3$+R$^4$ together also denote C$_1$-C$_6$-alkylene, in particular of the formula —CH$_2$—(CH$_2$)$_p$—CH$_2$— or —C(CH$_3$)$_2$C(CH$_3$)$_2$—, or 1,2-phenylene, where R$^3$, R$^4$ and R$^3$+R$^4$ may also be substituted, in particular by C$_1$-C$_6$-alkyl, F, Cl, C$_1$-C$_6$-alkoxy, and where p is 0 or 1, is reacted with a compound of the formula III

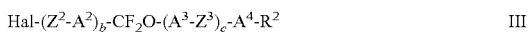

Hal-(Z$^2$-A$^2$)$_b$-CF$_2$O-(A$^3$-Z$^3$)$_c$-A$^4$-R$^2$   III in which Z$^2$, Z$^3$, A$^2$, A$^3$, A$^4$, b, c and R$^2$ are as defined in claim 1, and Hal denotes OSO$_2$CF$_3$, Cl, Br or I, in the presence of a transition-metal catalyst, preferably a palladium complex. The complexes are preferably palladium (II) complexes, in particular bis(triphenylphosphine)palladium(II) chloride. Hal preferably denotes chlorine or bromine, in particular bromine. In formula III, b preferably denotes 1 or 2 and Z$^2$ preferably denotes a single bond. The radical Hal is preferably bonded directly to a radical A$^2$. A$^2$ preferably denotes an aromatic ring system. Preference is furthermore given to the sub-forms indicated for the compounds of the formula I.

Further preferred process variants are revealed by the examples, the details of which—also generalised in accordance with general expert knowledge—are representative of preferred embodiments of the process according to the invention and the products thereof.

The invention also relates to liquid-crystalline media comprising one or more of the compounds of the formula I according to the invention. The liquid-crystalline media comprise at least two components, preferably one or more compounds of the formula I and at least one further compound, which is preferably mesogenic. The media according to the invention are preferably obtained by mixing the components with one another. A process according to the invention for the preparation of a liquid-crystalline medium is therefore characterised in that at least one compound of the formula I is mixed with at least one further mesogenic compound, and additives are optionally added.

The achievable combinations of clearing point, viscosity at low temperature, thermal/UV stability and high dielectric and optical anisotropy are superior to previous materials from the prior art. At the same time, low threshold voltages, good VHR values (VHR: 'voltage holding ratio') and good low-temperature stability are achieved.

Besides one or more compounds according to the invention, the liquid-crystalline media according to the invention preferably comprise, as further constituents, 2 to 40, particularly preferably 4 to 30, components. In particular, these media comprise 7 to 25 components besides one or more compounds according to the invention.

The liquid-crystal media according to the invention are prepared in a manner conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example through the use of pre-mixes, for example homologue mixtures, or using so-called "multibottle" systems.

The dielectrics may also comprise further additives known to the person skilled in the art and described in the literature. For example, 0 to 15%, preferably 0 to 10%, of pleochroic dyes, chiral dopants, stabilisers or nanoparticles may be added. The individual compounds added are employed in concentrations of 0.01 to 6%, preferably 0.1 to 3%. However, the concentration data for the remaining constituents of the liquid-crystal mixtures, i.e. the liquid-crystalline or mesogenic compounds, are indicated without taking into account the concentration of these additives. The liquid-crystal media according to the invention enable a significant broadening of the available parameter latitude.

The invention also relates to electro-optical displays (in particular TFT displays having two plane-parallel outer plates, which, together with a frame, form one or more cells, integrated non-linear elements for switching individual pixels on the outer plates, and a nematic liquid-crystal mixture having positive dielectric anisotropy and high specific resistance which is located in the cell), which contain media of this type, and to the use of these media for electro-optical purposes.

The total amount of compounds of the formula I in the mixtures according to the invention is not crucial. The mixtures can therefore comprise one or more further components for the purposes of optimisation of various properties. However, the observed effect on the addressing times and the threshold voltage is generally greater, the higher the total concentration of compounds of the formula I.

Particularly preferred LC media according to the invention are mentioned below:

LC medium which additionally comprises one or more compounds of the formulae II and/or III:

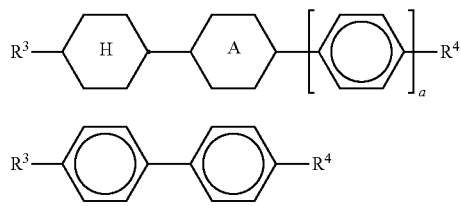

in which
ring A denotes 1,4-phenylene or trans-1,4-cyclohexylene,
a is 0 or 1,
$R^3$ in each case, independently of one another, denotes alkyl having 1 to 9 C atoms or alkenyl having 2 to 9 C atoms, preferably alkenyl having 2 to 9 C atoms, and
$R^4$ in each case, independently of one another, denotes an unsubstituted or halogenated alkyl radical having 1 to 12 C atoms, where, in addition, one or two non-adjacent $CH_2$ groups may be replaced by —O—, —CH=CH—, —CH=CF—, —(CO)—, —O(CO)— or —(CO)O— in such a way that O atoms are not linked directly to one another, and preferably denotes alkyl having 1 to 12 C atoms or alkenyl having 2 to 9 C atoms.

The compounds of the formula II are preferably selected from the group consisting of the following formulae:

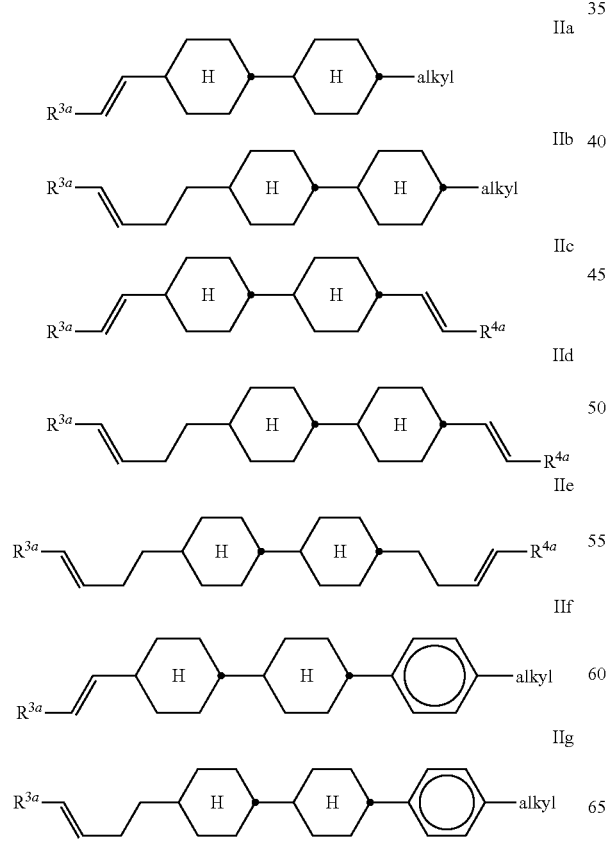

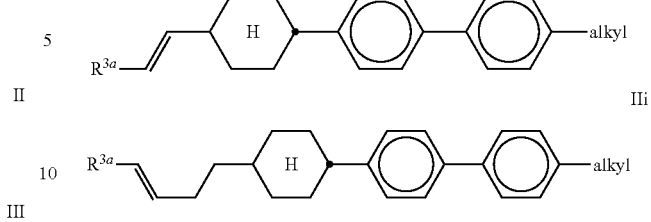

in which $R^{3a}$ and $R^{4a}$ each, independently of one another, denote H, $CH_3$, $C_2H_5$ or $C_3H_7$, and "alkyl" denotes a straight-chain alkyl group having 1 to 8, preferably 1, 2, 3, 4 or 5, C atoms. Particular preference is given to compounds of the formulae IIa and IIf, in particular those in which $R^{3a}$ denotes H or $CH_3$, preferably H, and compounds of the formula IIc, in particular those in which $R^{3a}$ and $R^{4a}$ denote H, $CH_3$ or $C_2H_5$.

The compounds of the formula III are preferably selected from the group consisting of the following formulae:

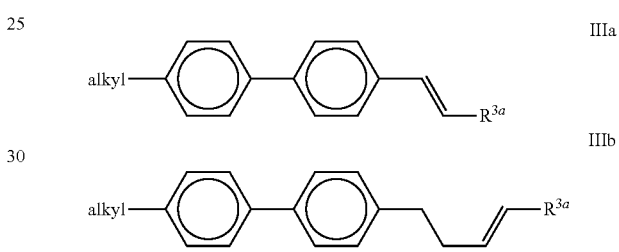

in which "alkyl" and $R^{3a}$ have the meanings indicated above, and $R^{3a}$ preferably denotes H or $CH_3$. Particular preference is given to compounds of the formula IIIb;

LC medium which additionally comprises one or more compounds selected from the group consisting of the following formulae:

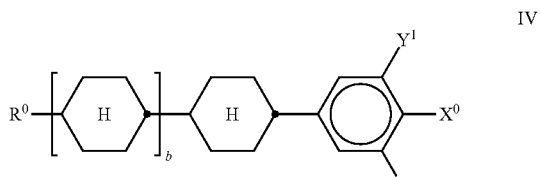

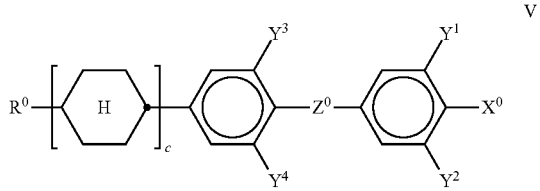

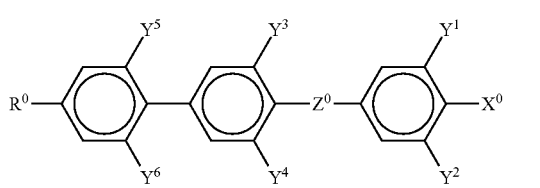

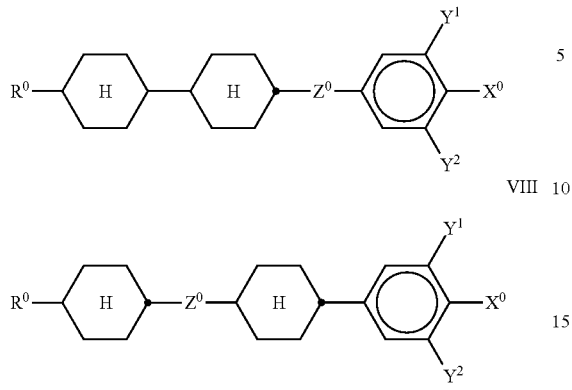

VII

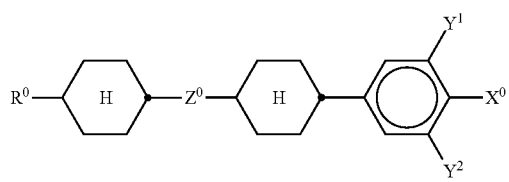

VIII in which

R⁰ denotes an alkyl or alkoxy radical having 1 to 15 C atoms, where, in addition, one or more CH₂ groups in these radicals may each be replaced, independently of one another, by —C≡C—, —CF₂O—, —CH=CH—, -◊-, -◊ ◊-, —O—, —(CO)O— or —O(CO)— in such a way that O atoms are not linked directly to one another, and in which, in addition, one or more H atoms may be replaced by halogen, X⁰ denotes F, Cl, CN, SF₅, SCN, NCS, a halogenated alkyl radical, halogenated alkenyl radical, halogenated alkoxy radical or halogenated alkenyloxy radical, each having up to 6 C atoms, Y$^{1-6}$ each, independently of one another, denote H or F, Z⁰ denotes —C₂H₄—, —(CH₂)₄—, —CH=CH—, —CF=CF—, —C₂F₄—, —CH₂CF₂—, —CF₂CH₂—, —CH₂O—, —OCH₂—, —COO—, —CF₂O— or —OCF₂—, in the formulae V and VI also a single bond, and b and c each, independently of one another, denote 0 or 1.

In the compounds of the formulae IV to VIII, X⁰ preferably denotes F or OCF₃, furthermore OCHF₂, CF₃, CF₂H, Cl, OCH=CF₂. R⁰ is preferably straight-chain alkyl or alkenyl, each having up to 6 C atoms.

The compounds of the formula IV are preferably selected from the group consisting of the following formulae:

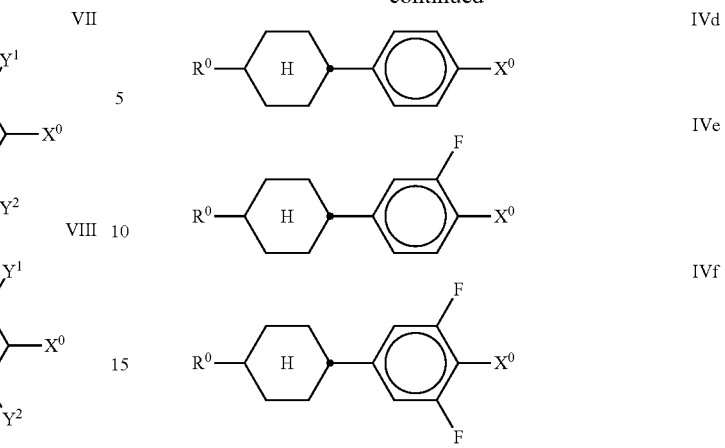

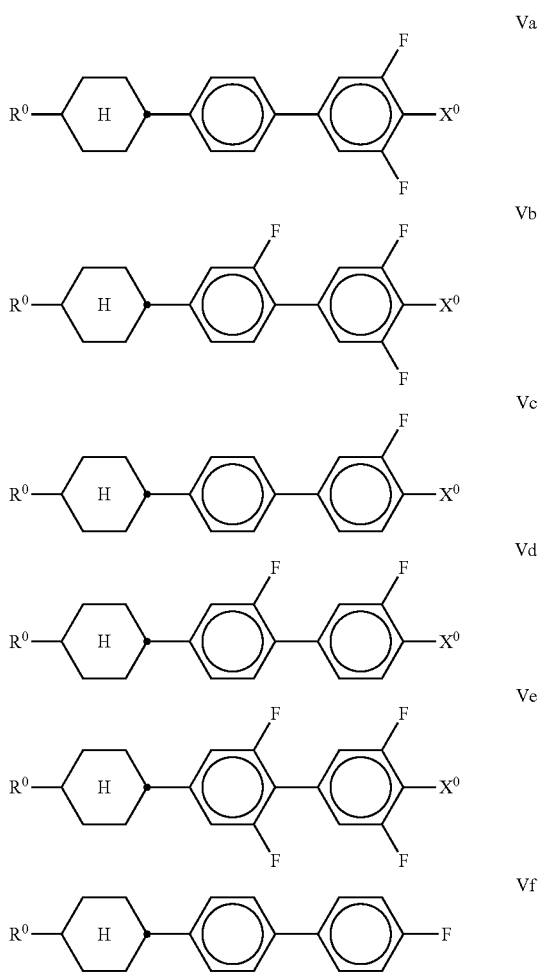

in which R⁰ and X⁰ have the meanings indicated above.

Preferably, R⁰ in formula IV denotes alkyl having 1 to 8 C atoms and X⁰ denotes F, Cl, OCHF₂ or OCF₃, furthermore OCH=CF₂. In the compound of the formula IVb, R⁰ preferably denotes alkyl or alkenyl. In the compound of the formula IVd, X⁰ preferably denotes Cl, furthermore F.

The compounds of the formula V are preferably selected from the group consisting of the following formulae:

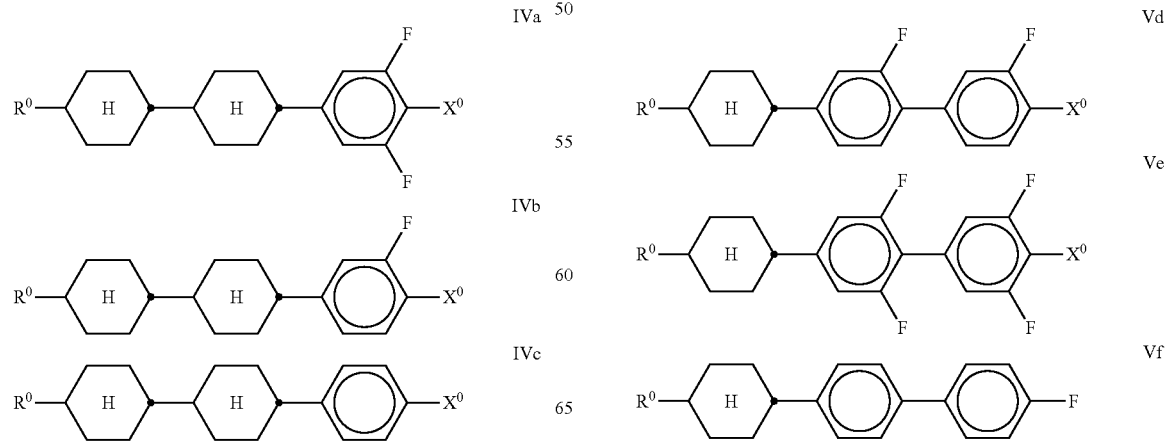

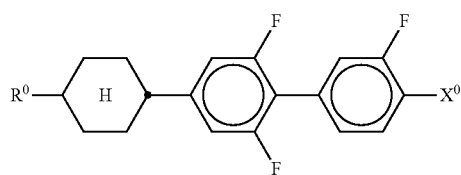
Vg in which $R^0$ and $X^0$ have the meanings indicated above. Preferably, $R^0$ in formula V denotes alkyl having 1 to 8 C atoms and $X^0$ denotes F;

LC medium which comprises one or more compounds of the formula VI-1:

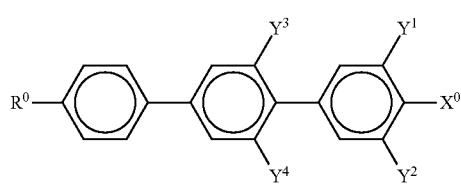
VI-1 particularly preferably those selected from the group consisting of the following formulae:

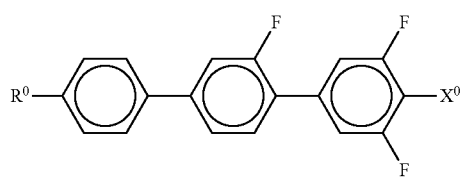
VI-1a

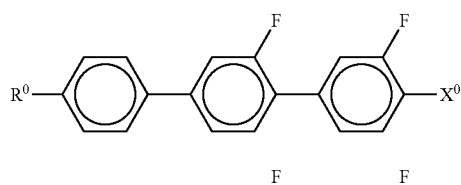
VI-1b

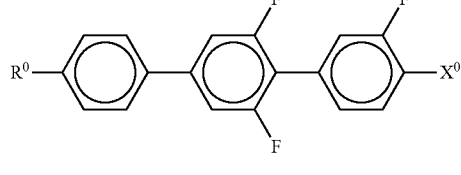
VI-1c

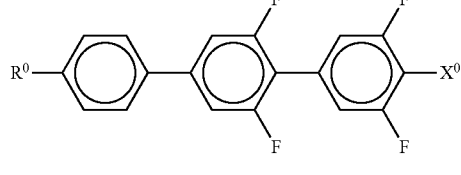
VI-1d in which $R^0$ and $X^0$ have the meanings indicated above. Preferably, $R^0$ in formula VI denotes alkyl having 1 to 8 C atoms and $X^0$ denotes F, furthermore $OCF_3$.

LC medium which comprises one or more compounds of the formula VI-2:

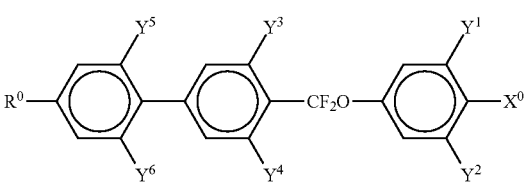
VI-2 particularly preferably those selected from the group consisting of the following formulae:

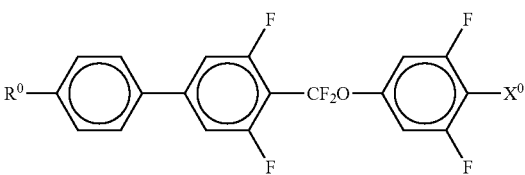
VI-2a

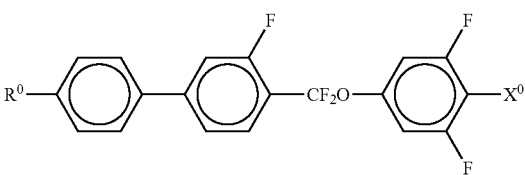
VI-2b

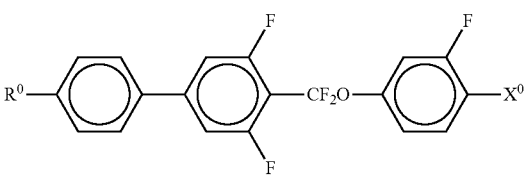
VI-2c

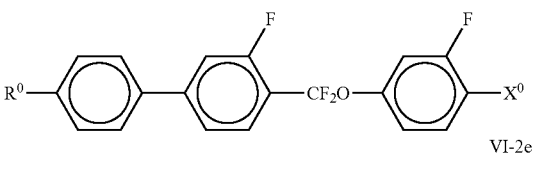
VI-2d

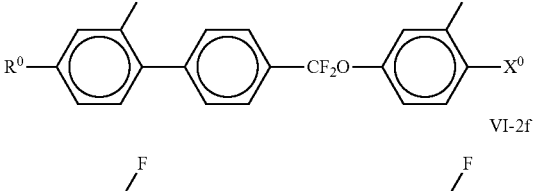
VI-2e

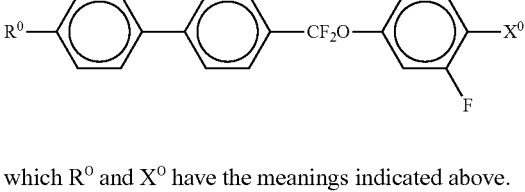
VI-2f in which $R^0$ and $X^0$ have the meanings indicated above. Preferably, $R^0$ in formula VI denotes alkyl having 1 to 8 C atoms and $X^0$ denotes F;

LC medium which preferably comprises one or more compounds of the formula VII in which $Z^0$ denotes —CF$_2$O—, —CH$_2$CH$_2$— or —(CO)O—, particularly preferably those selected from the group consisting of the following formulae:

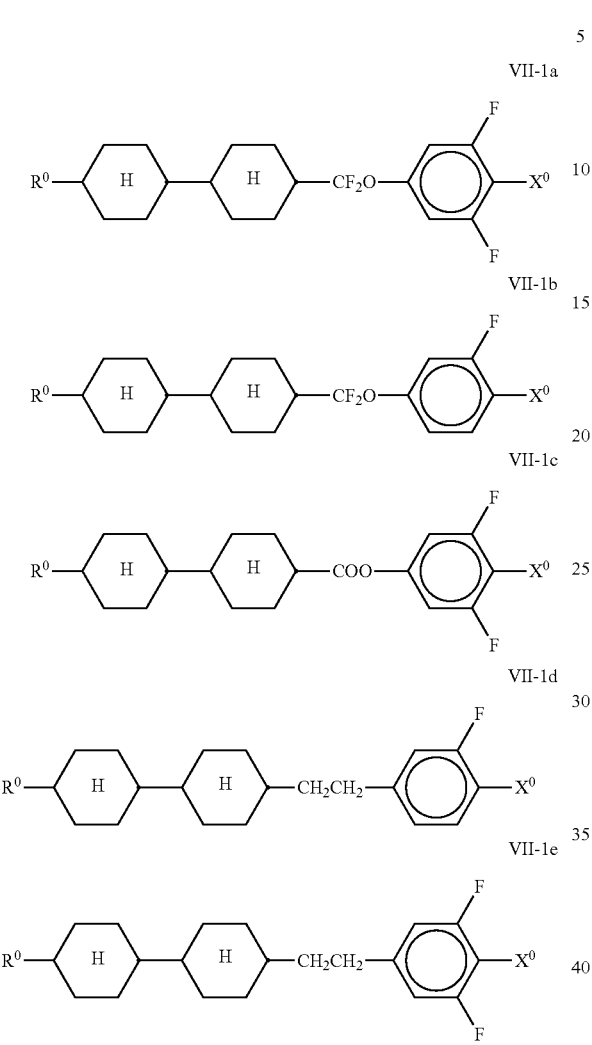

VII-1a
VII-1b
VII-1c
VII-1d
VII-1e in which R$^0$ and X$^0$ have the meanings indicated above. Preferably, R$^0$ in formula VII denotes alkyl having 1 to 8 C atoms and X$^0$ denotes F, furthermore OCF$_3$.

The compounds of the formula VIII are preferably selected from the group consisting of the following formulae:

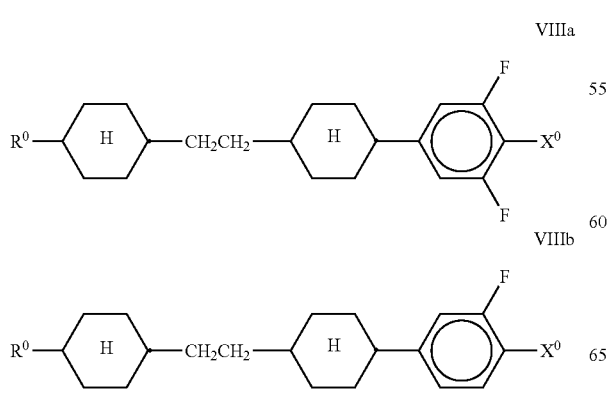

VIIIa
VIIIb

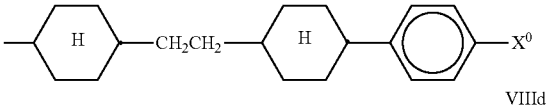

VIIIc

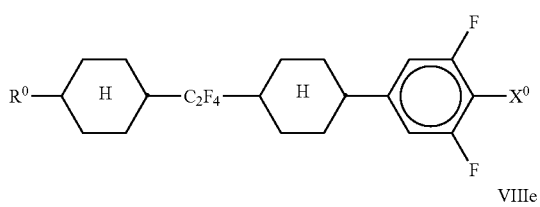

VIIId
VIIIe

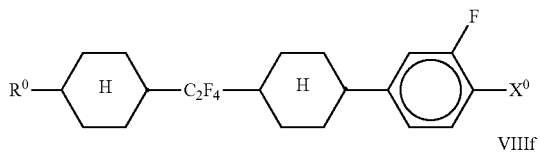

VIIIf

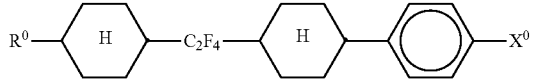

in which R$^0$ and X$^0$ have the meanings indicated above. R$^0$ preferably denotes a straight-chain alkyl radical having 1 to 8 C atoms. X$^0$ preferably denotes F.

LC medium which additionally comprises one or more compounds of the following formula:

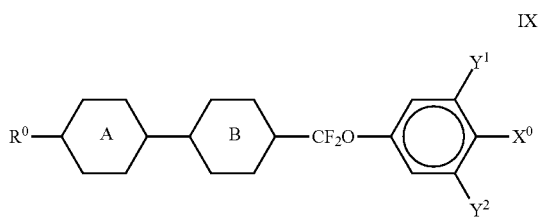

IX in which R$^0$, X$^0$, Y$^1$ and Y$^2$ have the meaning indicated above, and

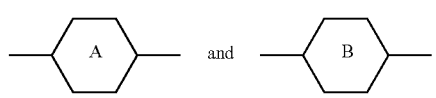

each, independently of one another, denote

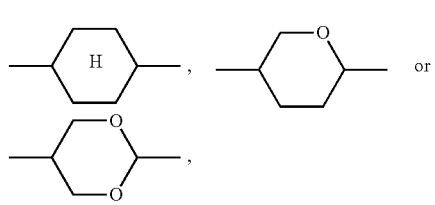

where the rings A and B do not both simultaneously denote cyclohexylene.

The compounds of the formula IX are preferably selected from the group consisting of the following formulae:

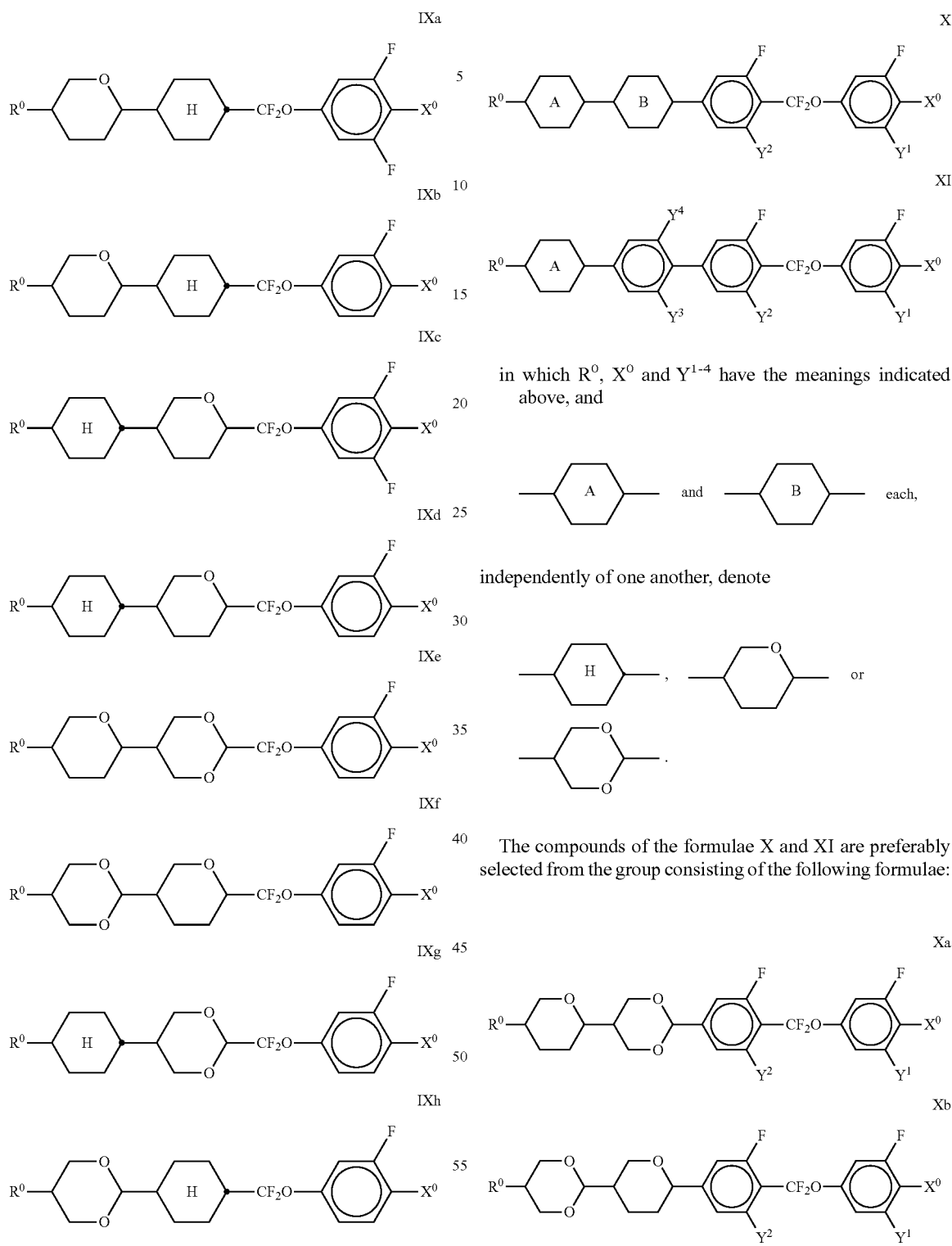

in which $R^0$, $X^0$ and $Y^{1-4}$ have the meanings indicated above, and

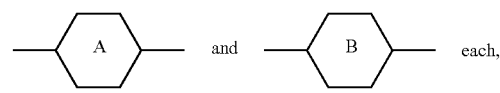

independently of one another, denote

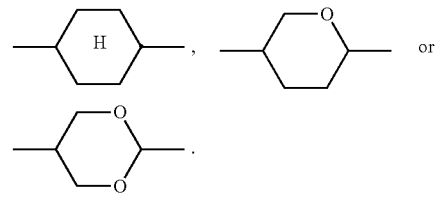

The compounds of the formulae X and XI are preferably selected from the group consisting of the following formulae:

in which $R^0$ and $X^0$ have the meanings indicated above. Preferably, $R^0$ denotes alkyl having 1 to 8 C atoms and $X^0$ denotes F. Particular preference is given to compounds of the formula IXa;

LC medium which additionally comprises one or more compounds selected from the group consisting of the following formulae:

-continued

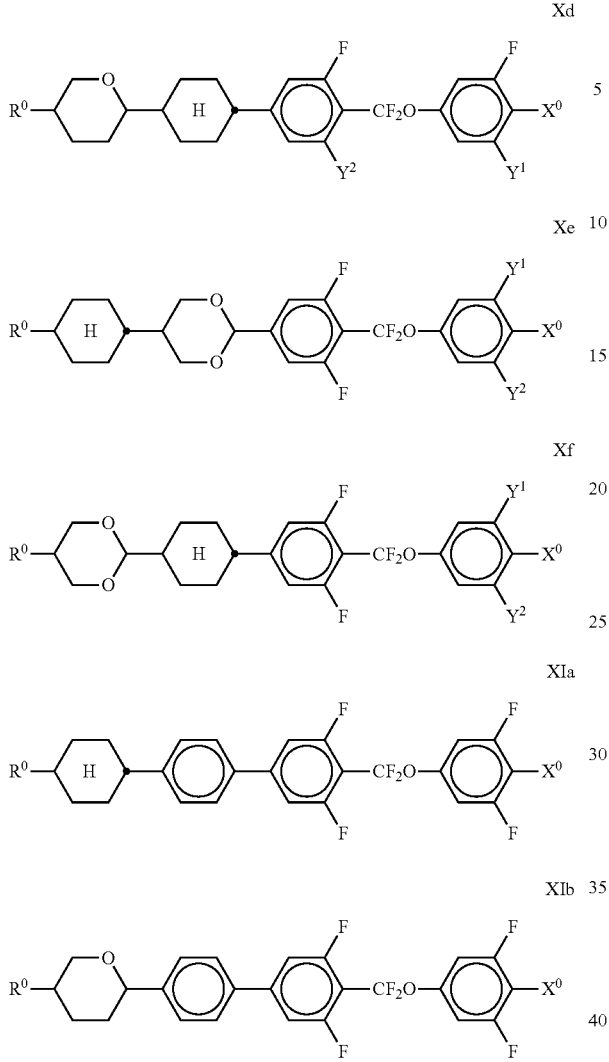

in which $R^0$ and $X^0$ have the meanings indicated above. Preferably, $R^0$ denotes alkyl having 1 to 8 C atoms and/or $X^0$ denotes F. Particularly preferred compounds are those in which $Y^1$ denotes F and $Y^2$ denotes H or F, preferably F;

LC medium which additionally comprises one or more compounds of the following formula XII:

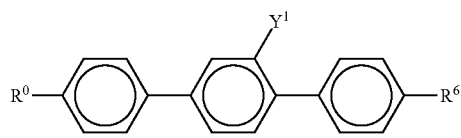

in which $R^5$ and $R^6$ each, independently of one another, denote n-alkyl, alkoxy, oxaalkyl, fluoroalkyl or alkenyl, each having up to 9 C atoms, and preferably each, independently of one another, denote alkyl having 1 to 7 C atoms or alkenyl having 2 to 7 C atoms. $Y^1$ denotes H or F.

Preferred compounds of the formula XII are those selected from the group consisting of the following formulae:

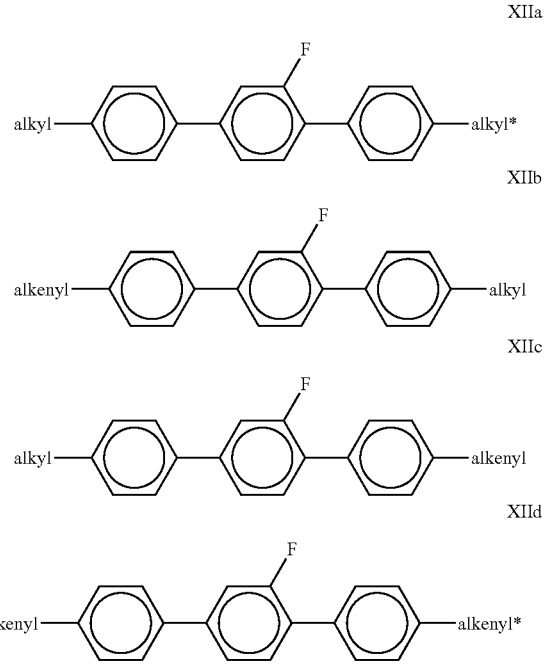

in which alkyl and alkyl* each, independently of one another, denote a straight-chain alkyl radical having 1 to 6 C atoms, and alkenyl and alkenyl* each, independently of one another, denote a straight-chain alkenyl radical having 2 to 6 C atoms.

Very particular preference is given to compounds of the following formula:

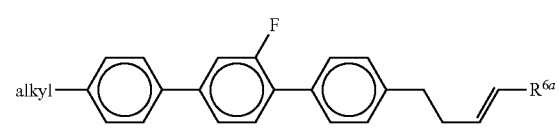

in which alkyl has the meaning indicated above and $R^{6a}$ denotes H or $CH_3$.

LC medium which additionally comprises one or more compounds selected from the group consisting of the following formulae:

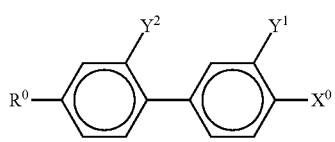

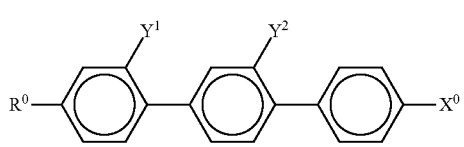

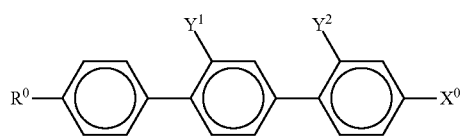

XV

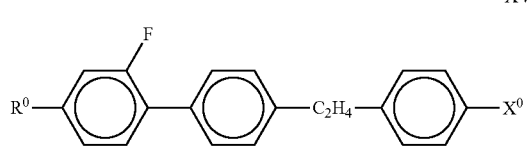

XVI in which $R^0$, $X^0$, $Y^1$ and $Y^2$ have the meanings indicated above. Preferably, $R^0$ denotes alkyl having 1 to 8 C atoms and $X^0$ denotes F or Cl.

The compounds of the formulae XIII and XIV are preferably selected from the group consisting of the following formulae:

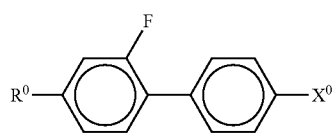

XIIIa

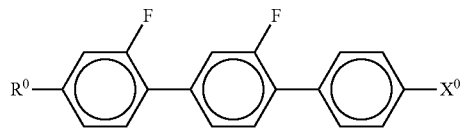

XIVa

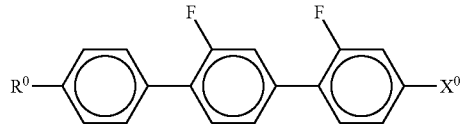

XVa in which $R^0$ and $X^0$ have the meanings indicated above. $R^0$ preferably denotes alkyl having 1 to 8 C atoms. In the compounds of the formula XIII, $X^0$ preferably denotes F or Cl.

LC medium which additionally comprises one or more compounds of the formulae D1 and/or D2:

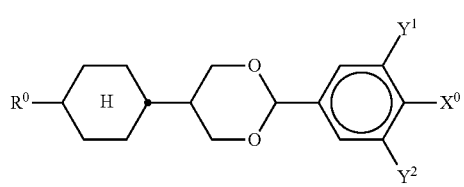

D1

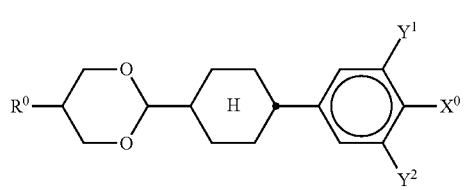

D2 in which $Y^1$, $Y^2$, $R^0$ and $X^0$ have the meaning indicated above. Preferably, $R^0$ denotes alkyl having 1 to 8 C atoms and $X^0$ denotes F. Particular preference is given to compounds of the following formulae:

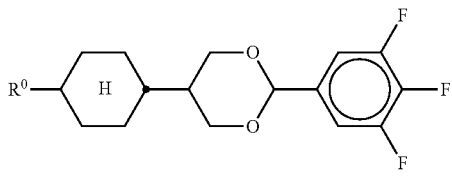

D1-1

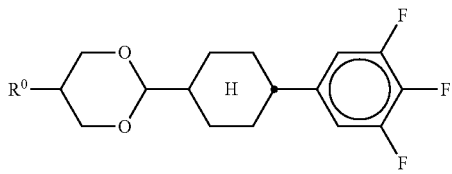

D2-1 in which $R^0$ has the meanings indicated above and preferably denotes straight-chain alkyl having 1 to 6 C atoms, in particular $C_2H_5$, n-$C_3H_7$ or n-$C_5H_{11}$.

LC medium which additionally comprises one or more compounds of the following formulae:

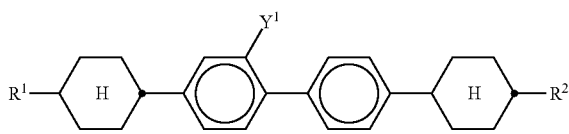

XVIIa

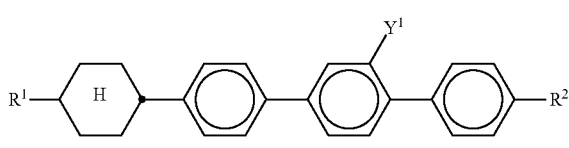

XVIIb in which $Y^1$, $R^1$ and $R^2$ have the meaning indicated above. $R^1$ and $R^2$ preferably each, independently of one another, denote alkyl having 1 to 8 C atoms. $Y^1$ preferably denotes F. Preferred media comprise 1-15% by weight, in particular 1-10% by weight, of these compounds.

LC medium which additionally comprises one or more compounds of the following formula:

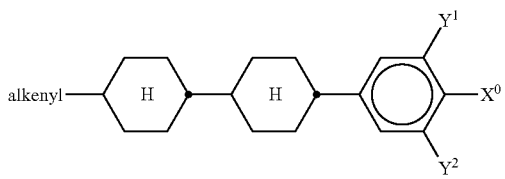

XVIII in which $X^0$, $Y^1$ and $Y^2$ have the meanings indicated above, and "alkenyl" denotes $C_{2-7}$-alkenyl. Particular preference is given to compounds of the following formula:

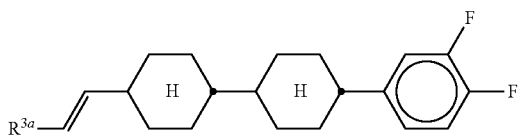

XVIIIa in which $R^{3a}$ has the meaning indicated above and preferably denotes H;

LC medium which additionally comprises one or more tetracyclic compounds selected from the group consisting of the formulae XIX to XXV:

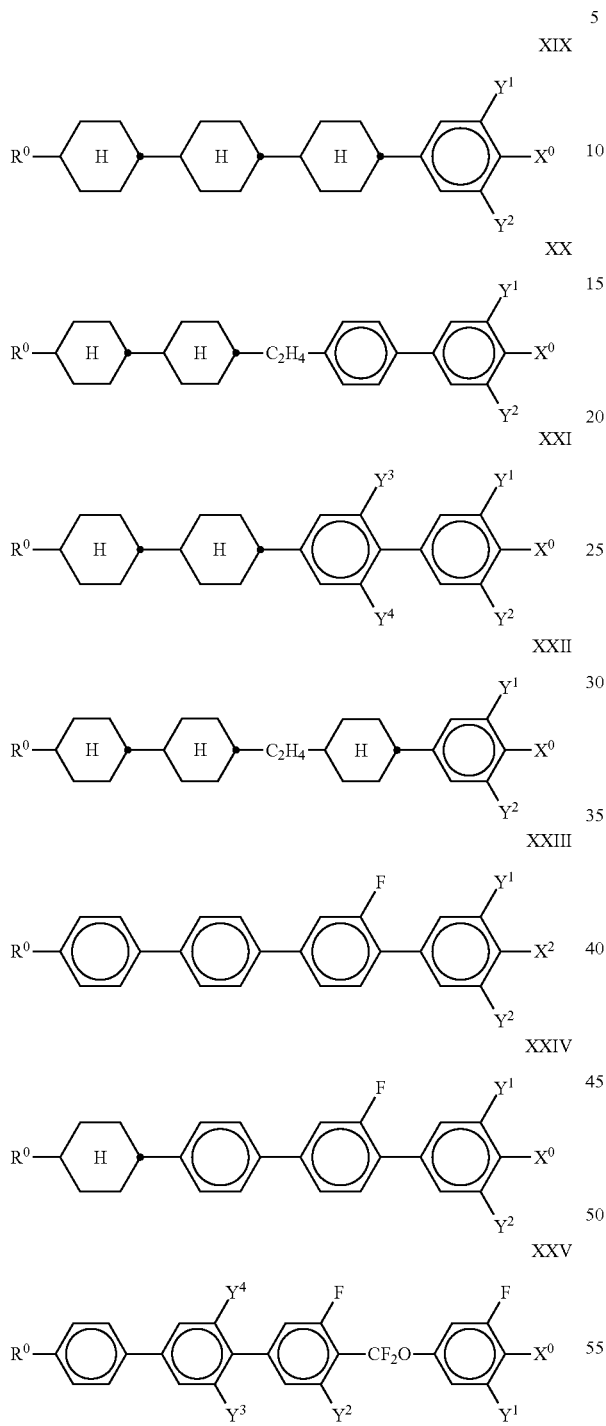

in which $Y^{1-4}$, $R^0$ and $X^0$ each, independently of one another, have one of the meanings indicated above. $X^0$ is preferably F, Cl, $CF_3$, $OCF_3$ or $OCHF_2$. $R^0$ preferably denotes alkyl, alkoxy, oxaalkyl, fluoroalkyl or alkenyl, each having up to 8 C atoms.

LC medium which additionally comprises one or more compounds of the following formula:

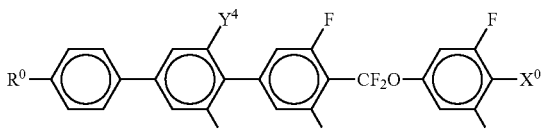

in which $R^0$, $X^0$ and $Y^{1-4}$ have the meanings indicated above. Particular preference is given to compounds of the following formula:

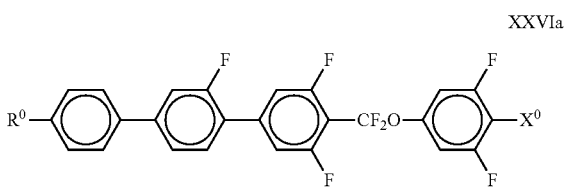

LC medium which additionally comprises one or more compounds of the following formula:

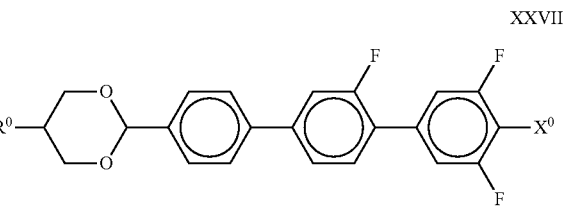

in which $R^0$, $Y^1$, $Y^2$ and $X^0$ are as defined above. $R^0$ particularly preferably denotes an n-butyl radical.

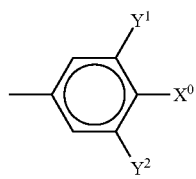

is preferably

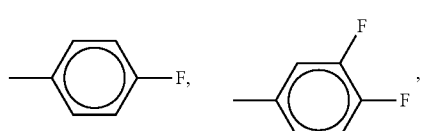

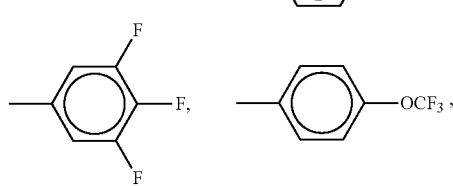

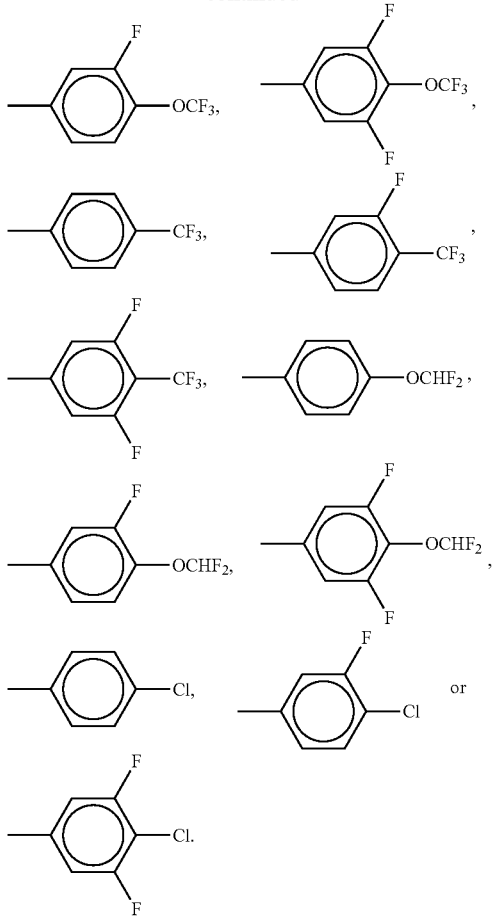

$R^0$ is generally preferably straight-chain alkyl or alkenyl having 2 to 7 C atoms;

$X^0$ is preferably F, furthermore $OCF_3$, $C_1$ or $CF_3$;

the medium preferably comprises one, two or three compounds of the formula I;

the medium preferably comprises in each case one or more compounds selected from the group of the compounds of the formulae I and II;

the medium preferably comprises one or more compounds selected from the group of the compounds of the formulae VI-2, VII-1a, VII-1b, IX, X, XI and XXV ($CF_2O$-bridged compounds); the total content of compounds of the formulae VI-2, VII-1a, VII-1b, IX, X, XI and XXV and of the compounds of the formula I according to the invention is preferably 35% by weight or more, particularly preferably 40% by weight or more and very particularly preferably 45% by weight or more;

the medium preferably comprises 1-25% by weight, preferably 10-20% by weight, of compounds of the formula I;

the proportion of compounds of the formulae II-XXVII in the mixture as a whole is preferably 20 to 99% by weight;

the medium preferably comprises 25-80% by weight, particularly preferably 30-70% by weight, of compounds of the formulae II and/or III;

the medium preferably comprises 20-70% by weight, particularly preferably 25-60% by weight, of compounds of the formula IIa;

the medium preferably comprises 2-25% by weight, particularly preferably 3-20% by weight, of compounds selected from the group of the compounds of the formulae I and VI-2; in a particularly preferred embodiment, a small proportion or no compound of the formula VI-2 is present. The compound of the formula I then completely or partly replaces this component;

the medium comprises in total 2-30% by weight, particularly preferably 3-20% by weight, of compounds of the formulae XI and XXVI together;

the medium preferably comprises 1-20% by weight, particularly preferably 2-15% by weight, of compounds of the formula XXIV;

the medium comprises in total 15-65% by weight, particularly preferably 30-55% by weight, of compounds selected from the highly polar compounds of the formulae VI-2, X, XI and XXVII together.

It has been found that even a relatively small proportion of compounds of the formula I mixed with conventional liquid-crystal materials, but in particular with one or more compounds of the formulae II to XXIX, results in a significant increase in the dielectric anisotropy and in low rotational viscosity values, with broad nematic phases having low smectic-nematic transition temperatures being observed at the same time, improving the storage stability. The media simultaneously exhibit very low threshold voltages and very good values for the VHR on exposure to UV.

The term "alkyl" encompasses straight-chain and branched alkyl groups having 1-9 carbon atoms, in particular the straight-chain groups methyl, ethyl, propyl, butyl, pentyl, hexyl and heptyl. Groups having 2-5 carbon atoms are generally preferred.

The term "alkenyl" encompasses straight-chain and branched alkenyl groups having up to 9 carbon atoms, in particular the straight-chain groups. Particularly preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" in this application encompasses straight-chain groups containing at least one fluorine atom, preferably a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "halogenated alkyl radical" preferably encompasses mono- or polyfluorinated and/or -chlorinated radicals. Perhalogenated radicals are included. Particular preference is given to fluorinated alkyl radicals, in particular $CF_3$, $CH_2CF_3$, $CH_2CHF_2$, $CHF_2$, $CH_2F$, $CHFCF_3$ and $CF_2CHFCF_3$.

The term "alkylene" encompasses straight-chain or branched alkanediyl groups having 1-12 carbon atoms, in particular the straight-chain groups methylene, ethylene, propylene, butylene and pentylene. Groups having 2-8 carbon atoms are generally preferred.

The term "oxaalkyl" or "alkoxy" in this application encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

If $R^0$ in the formulae above and below denotes an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If $R^0$ denotes an alkyl radical in which a $CH_2$ group has been replaced by —CH=CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl. These radicals may also be mono- or polyhalogenated.

If $R^0$ denotes an alkyl or alkenyl radical which is at least monosubstituted by halogen, this radical is preferably straight-chain and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the co-position.

In the formulae above and below, $X^0$ is preferably F, Cl or a mono- or polyfluorinated alkyl or alkoxy radical having 1, 2 or 3 C atoms or a mono- or polyfluorinated alkenyl radical having 2 or 3 C atoms. $X^0$ is particularly preferably F, Cl, $CF_3$, $CHF_2$, $OCF_3$, $OCHF_2$, $OCFHCF_3$, $OCFHCHF_2$, $OCFHCH_2F$, $OCF_2CH_3$, $OCF_2CHF_2$, $OCF_2CH_2F$, $OCF_2CF_2CHF_2$, $OCF_2CF_2CH_2F$, $OCFHCF_2CF_3$, $OCFHCF_2CHF_2$, $OCH=CF_2$, $OCF=CF_2$, $OCF_2CHFCF_3$, $OCF_2CF_2CF_3$, $OCF_2CF_2C\equiv ClF_2$, $OC\equiv ClFCF_2CF_3$, $CF=CF_2$, $CF=CHF$ or $CH=CF_2$, very particularly preferably F or $OCF_3$.

Through a suitable choice of the meanings of $R^0$ and $X^0$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals. The media according to the invention are distinguished, in particular, by high $K_1$ values and thus have significantly faster response times than the media from the prior art.

The optimum mixing ratio of the compounds of the above-mentioned formulae depends substantially on the desired properties, on the choice of the components of the above-mentioned formulae and on the choice of any further components that may be present.

Suitable mixing ratios within the range indicated above can easily be determined from case to case.

In a preferred embodiment of the media according to the invention, the dielectric anisotropy is 13 or more, preferably 17 or more. The optical anisotropy here is preferably between 0.10 or more and 0.14 or less, particularly preferably between 0.11 and 0.13. The clearing point here is preferably between 70° C. or more and 120° C. or less. The mixture is preferably stable down to −25° C. Media of this type have a very low threshold voltage. Media of this type preferably comprise 55% by weight or more of highly polar compounds having a dielectric anisotropy of 10 or more. They particularly preferably comprise 45% by weight or more of highly polar compounds having a dielectric anisotropy of 20 or more. Compounds of this type are generally selected from compounds of the formulae I, VI-2, X, XI and XXVII. Suitable individual compounds are given by comparison of the formulae I, VI-2, X, XI and XXVII with the examples.

In a further preferred embodiment of the media according to the invention, the rotational viscosity is 90 mPas or less, preferably 80 mPas or less. The optical anisotropy here is preferably between 0.08 or more and 0.14 or less, particularly preferably between 0.11 and 0.13. The clearing point here is preferably between 70° C. or more and 100° C. or less. Media of this type generally have a relatively fast response time. The proportion of compounds of the formula II is preferably 40% by weight or more, particularly preferably 45% by weight or more. In the case where no compounds of the formula II in which a=1 are employed, the proportion of compounds of the formula II in which a=0 is correspondingly increased. The proportion of non-polar compounds of the formulae IIa and IIb together is, in accordance with this embodiment, preferably greater than 30% by weight, particularly preferably 35% by weight or more. Accordingly, the proportion of compounds of the formula II in which a=1 can preferably be varied between 0 and 25% by weight or less.

The total amount of compounds of the above-mentioned formulae in the mixtures according to the invention is not crucial. The mixtures can therefore comprise one or more further components for the purposes of optimisation of various properties. However, the observed effect on the desired improvement in the properties of the mixture is generally greater, the higher the total concentration of compounds of the above-mentioned formulae.

The individual compounds of the above-mentioned formulae and the subformulae thereof which can be used in the media according to the invention are either known or methods for their preparation can readily be derived from the prior art by the person skilled in the relevant art since they are based on standard methods described in the literature.

The liquid-crystal media according to the invention enable a significant broadening of the available parameter latitude.

The media according to the invention are particularly suitable for mobile applications and high-Δn TFT applications, such as, for example, PDAs, notebooks, LCD TVs and monitors.

The liquid-crystal media according to the invention, with retention of the nematic phase down to −20° C. and preferably down to −30° C., particularly preferably down to −40° C., and of the clearing point 70° C., preferably ≥75° C., simultaneously enable rotational viscosities $\gamma_1$ of 110 mPa·s, particularly preferably ≤90 mPa·s, to be achieved, enabling excellent MLC displays having fast response times to be obtained.

The dielectric anisotropy Δ∈ of the liquid-crystal media according to the invention is preferably ≥+5, particularly preferably ≥+10. In addition, the media are characterised by low operating voltages. The threshold voltage of the liquid-crystal media according to the invention is preferably ≤1.4 V, in particular ≤1.2 V, in media adapted for the purpose also ≤1.0 V.

The birefringence Δn of the liquid-crystal media according to the invention is preferably ≥0.10, particularly preferably ≥0.11. Δn is preferably ≤0.15, particularly preferably ≤0.13

Further particularly preferred embodiments of the invention extend to the following parameters:

The nematic phase range of the liquid-crystal media according to the invention preferably has a width of at least 90°, in particular at least 100°. This range preferably extends at least from −25° C. or less to +70° C. or more, particularly preferably from −30 to 80° C. or higher. In a further preferred embodiment, the clearing point is between 70 and 100° C., particularly preferably between 75 and 90° C.

It goes without saying that, through a suitable choice of the components of the media according to the invention, it is also possible for higher clearing points (for example above 100° C.) to be achieved at higher threshold voltages or lower clearing points to be achieved at lower threshold voltages with retention of the other advantageous properties. At viscosities correspondingly increased only slightly, it is likewise possible to obtain media having a higher $\Delta\in$ and thus low thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (German patent 30 22 818), lower dielectric anisotropy is sufficient at the same threshold voltage as in an analogous display at the second minimum. This enables significantly higher specific resistance values to be achieved using the media according to the invention at the first minimum than in the case of media comprising cyano compounds. Through a suitable choice of the individual components and their proportions by weight, the person skilled in the art is able to set the birefringence necessary for a pre-specified layer thickness of the MLC display using simple routine methods.

Measurements of the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that media according to the invention comprising compounds of the formula I exhibit a significantly smaller decrease in the HR on UV exposure than analogous media comprising cyanophenylcyclohexanes of the formula

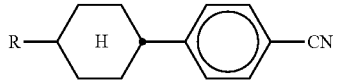

or esters of the formula

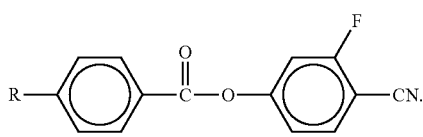

The LC media are preferably 99% by weight, particularly preferably 100% by weight, free from benzonitrile derivatives.

The LC media may also comprise further additives known to the person skilled in the art and described in the literature, such as, for example, UV stabilisers, such as Tinuvin® from Ciba, antioxidants, free-radical scavengers, nanoparticles, etc. For example, 0-15% of pleochroic dyes or chiral dopants can be added. Suitable dopants are mentioned below in Table C.

The LC media preferably comprise 0 to 10% by weight, in particular 0.01 to 5% by weight and particularly preferably 0.1 to 3% by weight, of stabilisers. The LC media preferably comprise one or more stabilisers selected from 2,6-di-tert-butylphenols, 2,2,6,6-tetramethylpiperidines and 2-benzotriazol-2-ylphenols. These assistants are known to the person skilled in the art and are commercially available, for example as light-protection agents.

The following examples explain the invention without intending to limit it. Above and below, percentage data denote percent by weight. All temperatures are indicated in degrees Celsius. Furthermore, Tg denotes glass transition temperature, C=crystalline state, N=nematic phase, Sm=smectic phase and I=isotropic phase. The data between these symbols represent the transition temperatures. An denotes optical anisotropy (589 nm, 20° C.), $\Delta\in$ the dielectric anisotropy (1 kHz, 20° C.), and $\gamma_1$ the rotational viscosity (in the unit mPa·s).

The substituents on the saturated 1,4-substituted ring systems drawn in the synthesis examples are, unless indicated otherwise, in the trans configuration. The other formulae stand for both configurations and preferably for the trans configuration In the present application and in the examples below, the structures of the liquid-crystal compounds are indicated by means of acronyms, with the transformation into chemical formulae taking place in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| nOCF$_3$ | $C_nH_{2n+1}$ | OCF$_3$ | H | H |
| nOCF$_3$.F | $C_nH_{2n+1}$ | OCFf$_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Preferred mixture components are found in Tables A and B.

TABLE A

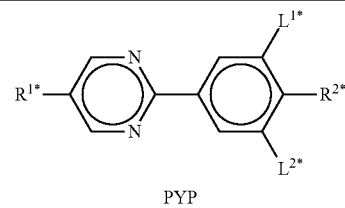

PYP

TABLE A-continued
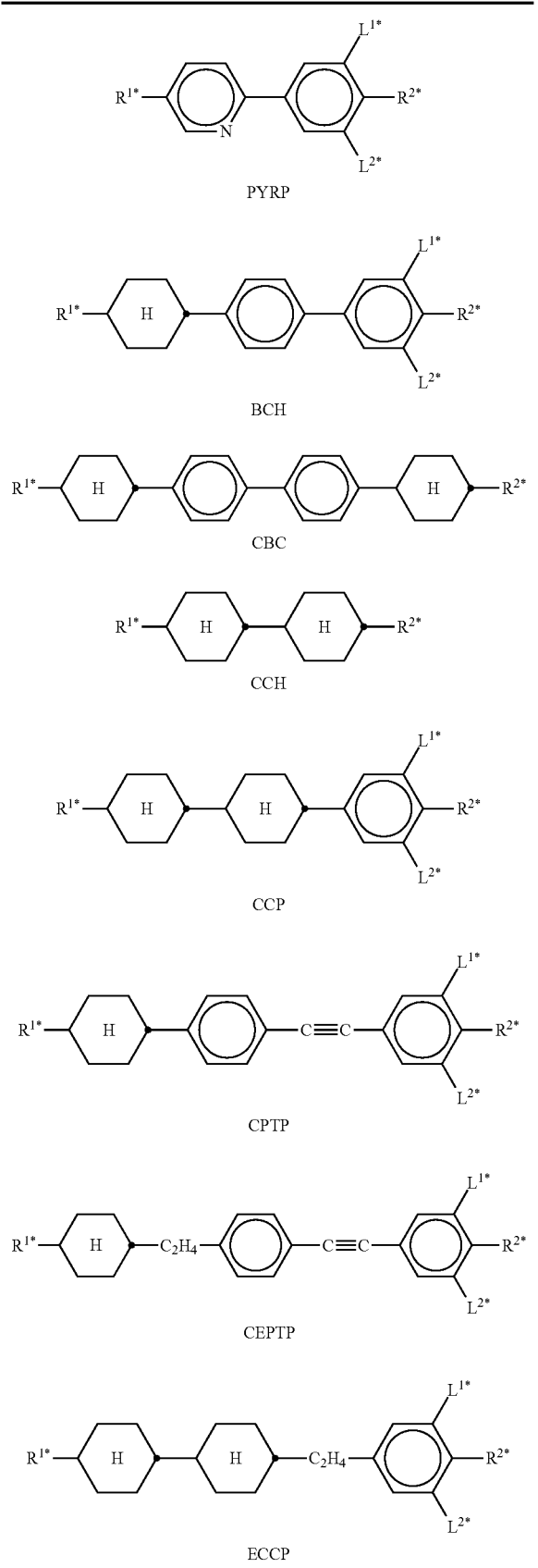
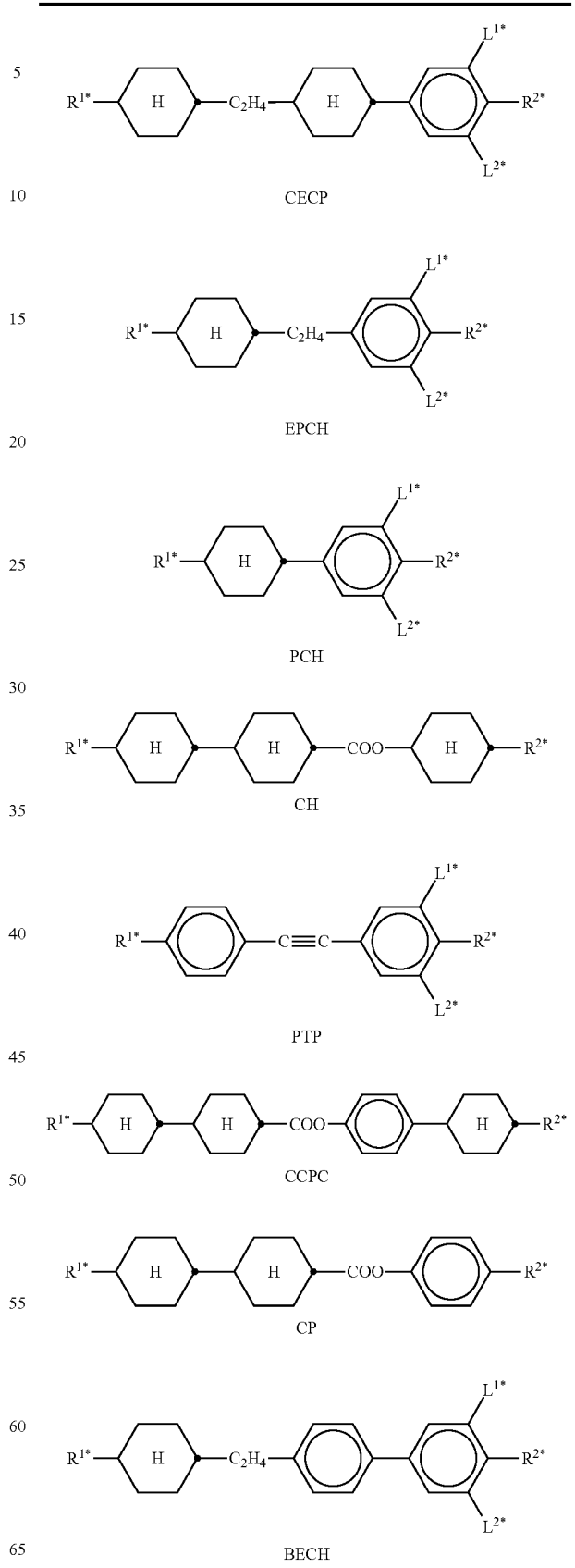

TABLE A-continued
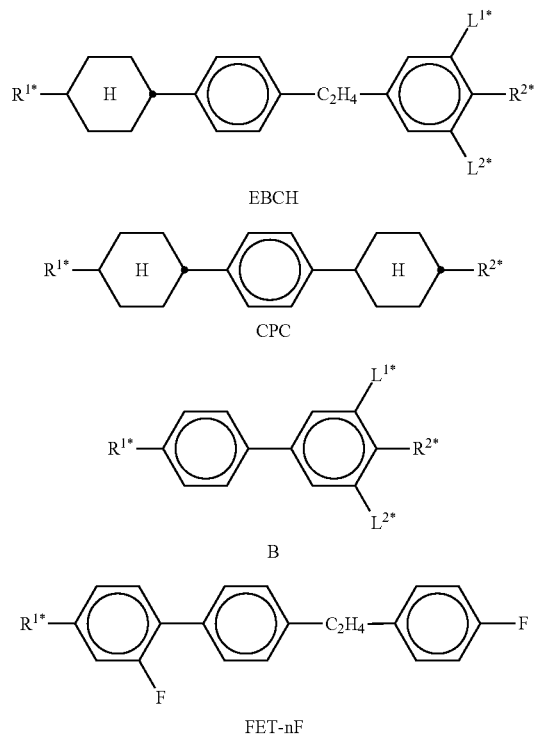
TABLE A-continued
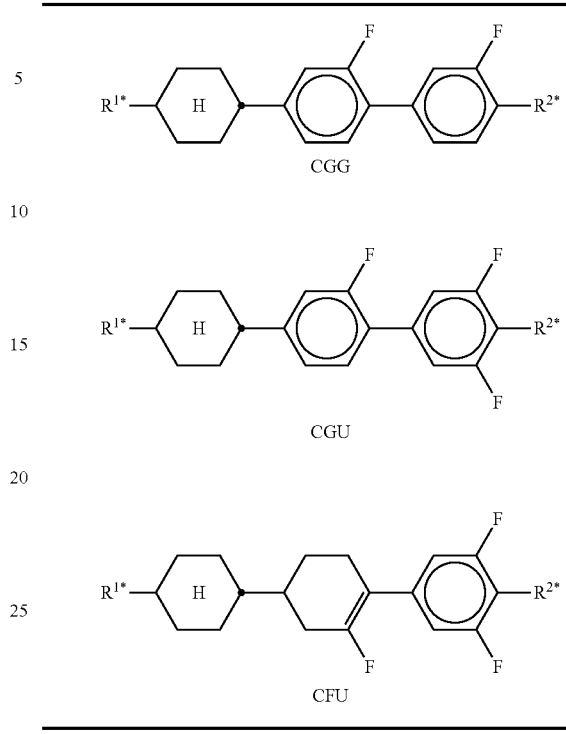
TABLE B
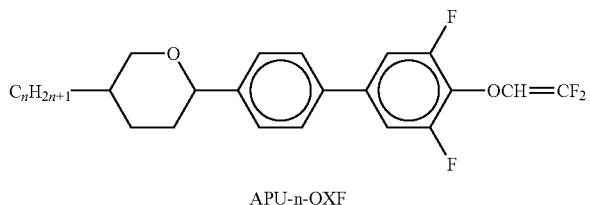
APU-n-OXF
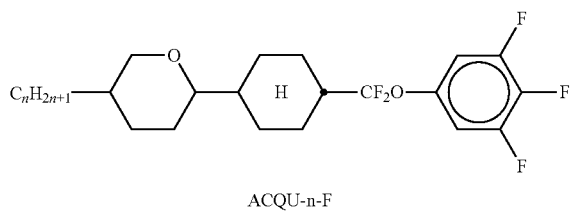
ACQU-n-F
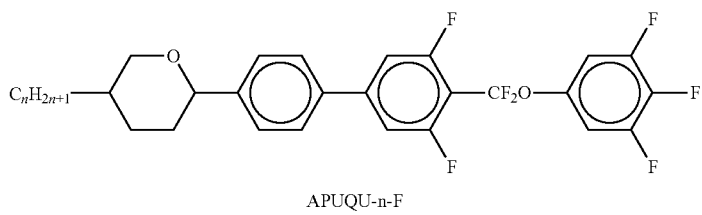
APUQU-n-F
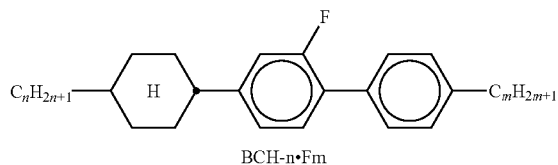
BCH-n·Fm TABLE B-continued
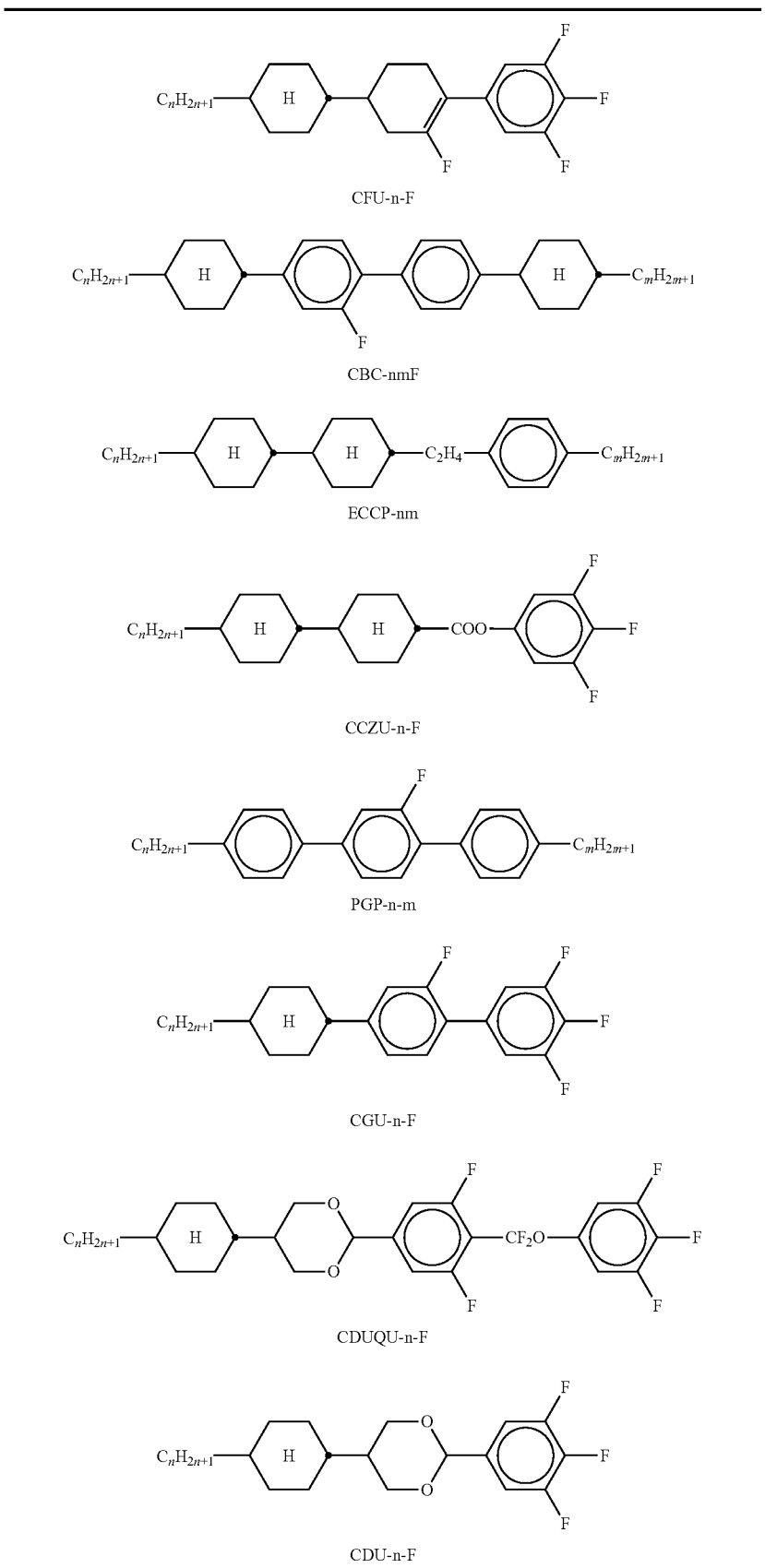

TABLE B-continued
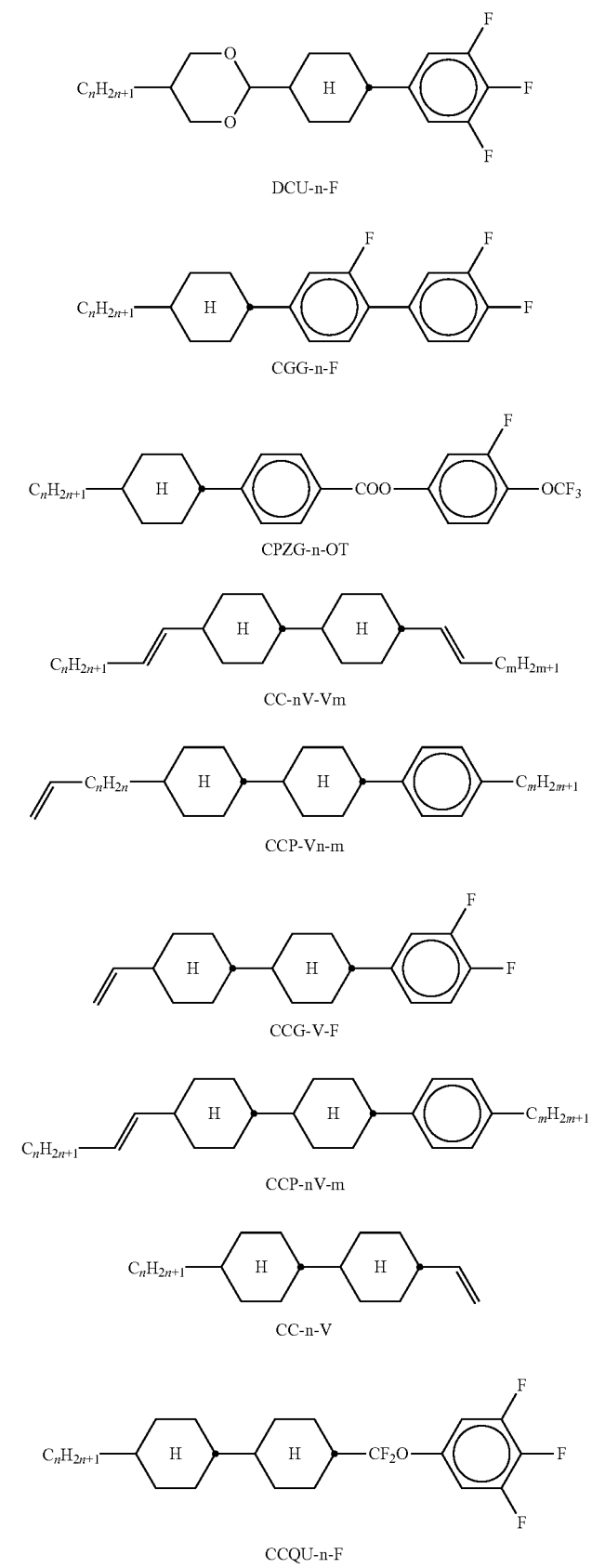

TABLE B-continued
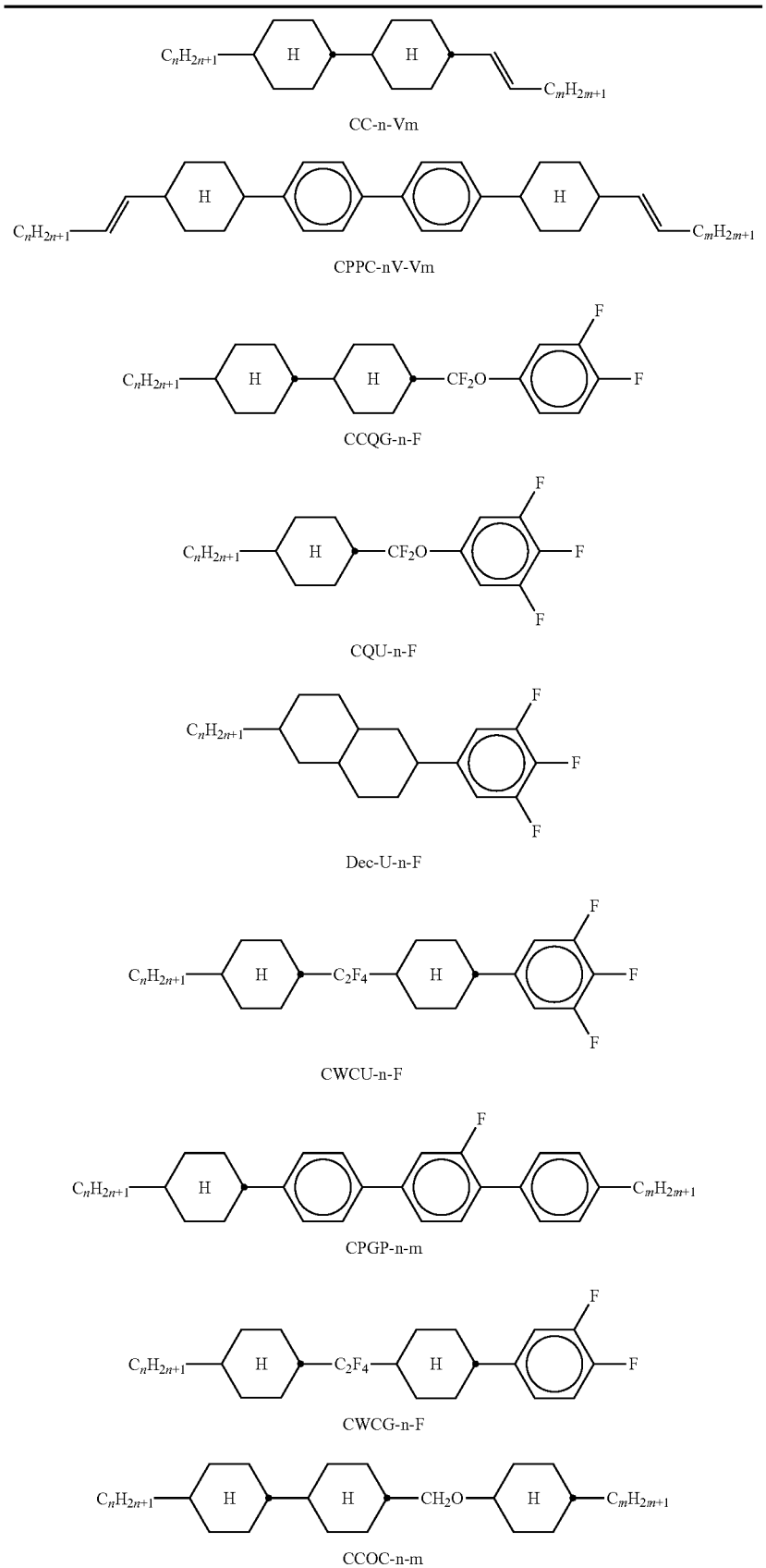

TABLE B-continued
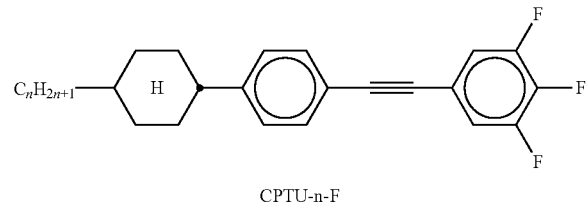
CPTU-n-F
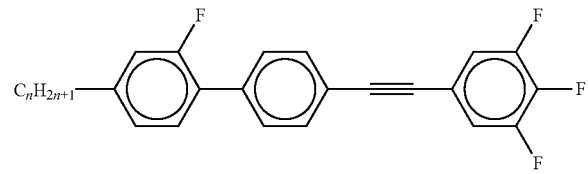
GPTU-n-F
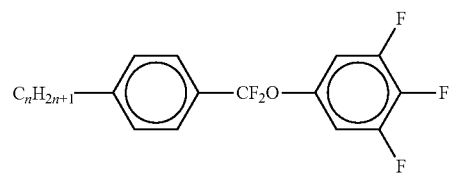
PQU-n-F
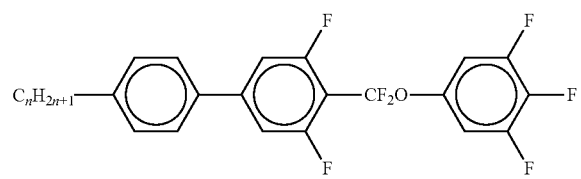
PUQU-n-F
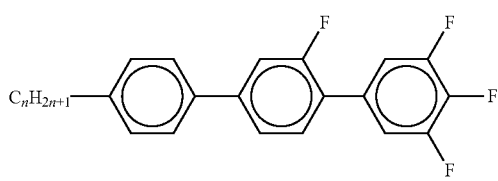
PGU-n-F
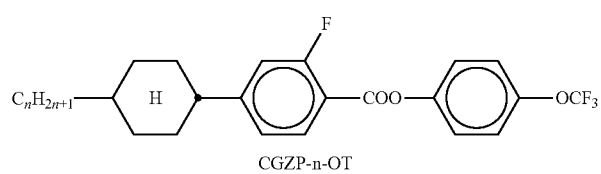
CGZP-n-OT
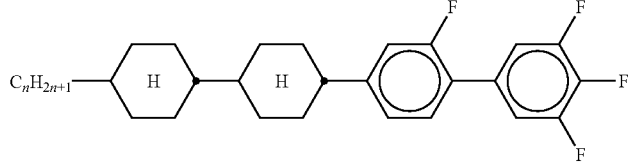
CCGU-n-F TABLE B-continued
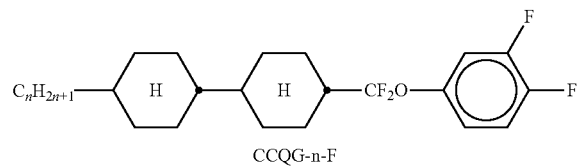
CCQG-n-F
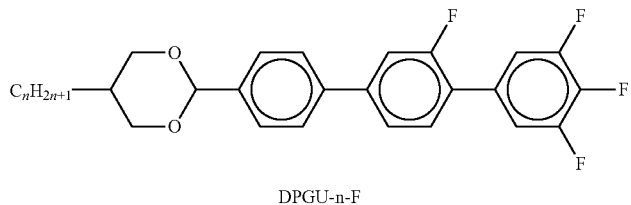
DPGU-n-F
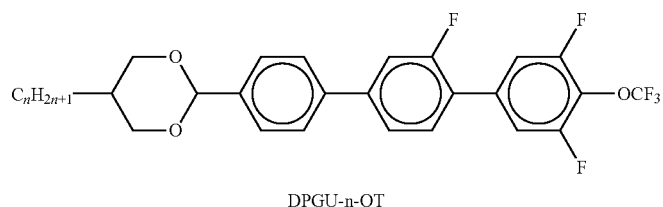
DPGU-n-OT
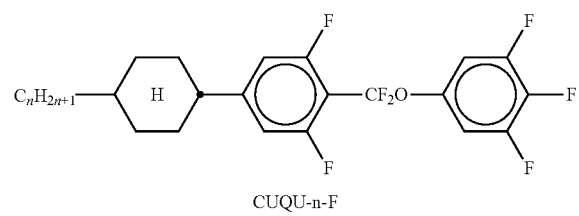
CUQU-n-F
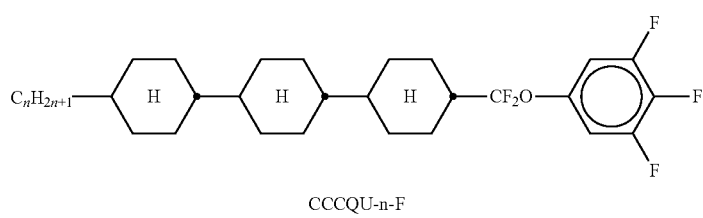
CCCQU-n-F
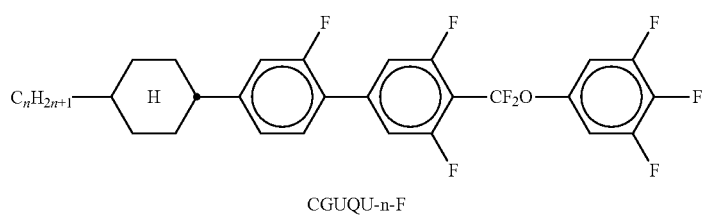
CGUQU-n-F
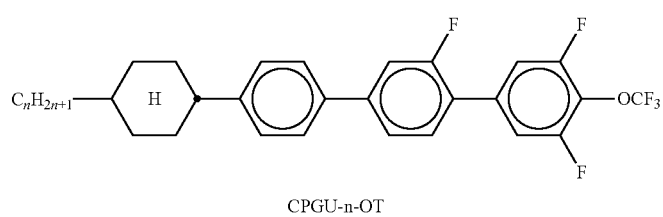
CPGU-n-OT
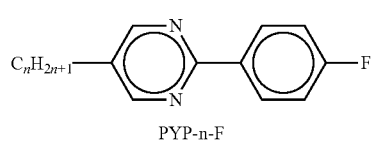
PYP-n-F TABLE B-continued
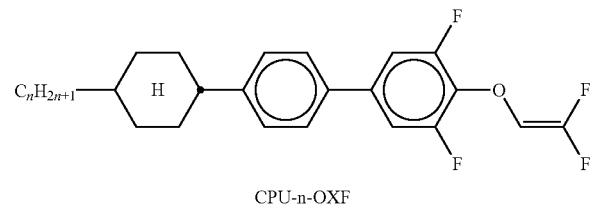
CPU-n-OXF
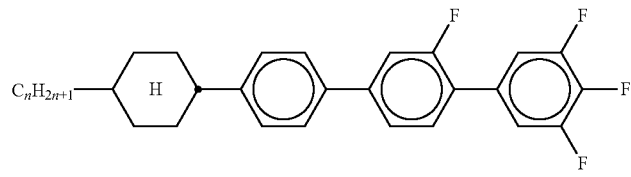
CPGU-n-F
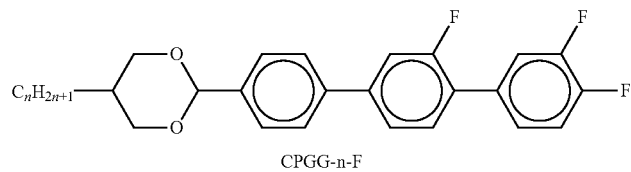
CPGG-n-F
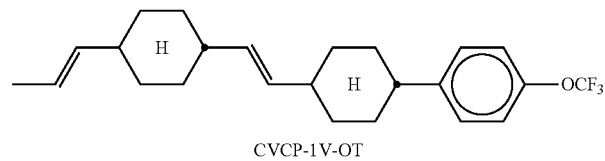
CVCP-1V-OT
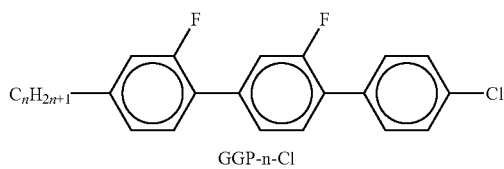
GGP-n-Cl
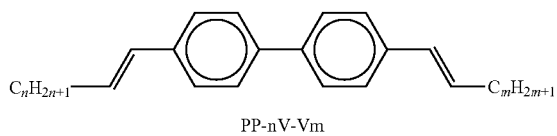
PP-nV-Vm
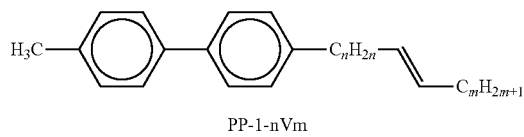
PP-1-nVm
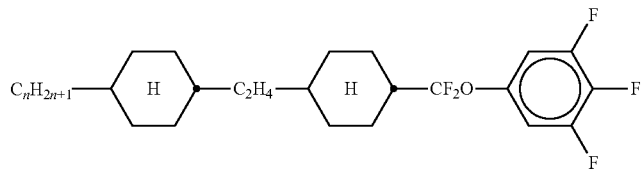
CWCQU-n-F TABLE B-continued
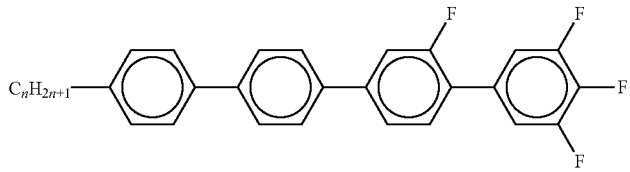
PPGU-n-F
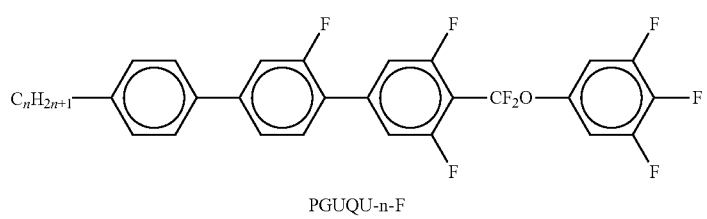
PGUQU-n-F
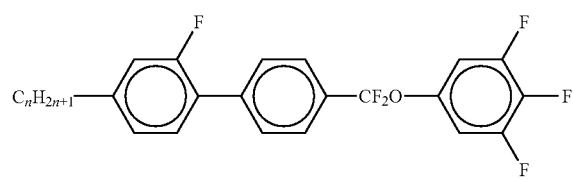
GPQU-n-F
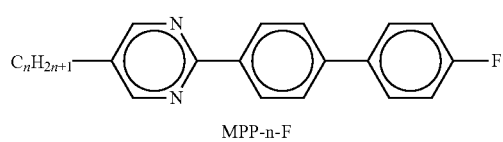
MPP-n-F
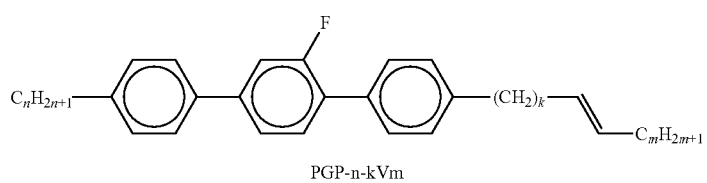
PGP-n-kVm
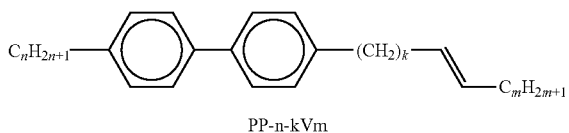
PP-n-kVm
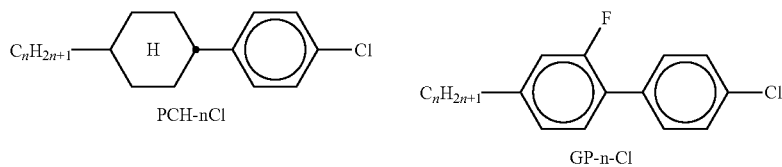
PCH-nCl         GP-n-Cl
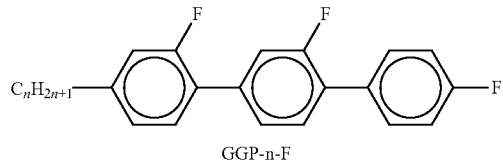
GGP-n-F TABLE B-continued
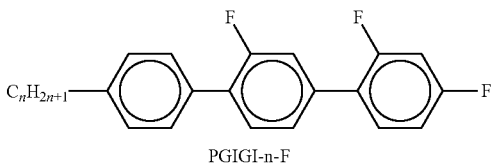
PGIGI-n-F
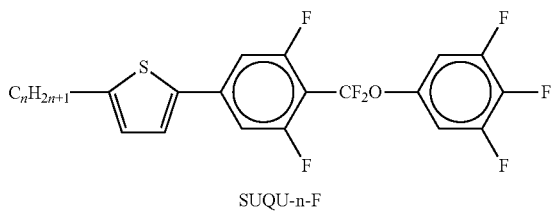
SUQU-n-F
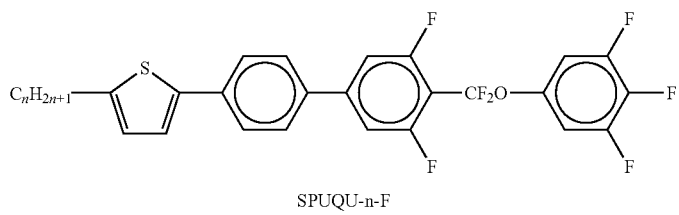
SPUQU-n-F
In a preferred embodiment of the present invention, the LC media according to the invention comprise one or more compounds selected from the group consisting of compounds from Tables A and B.
TABLE C
Table C indicate possible dopants which can be added to the LC media according to the invention.
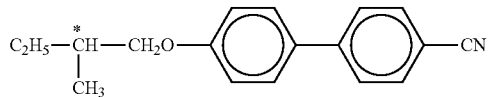
C 15
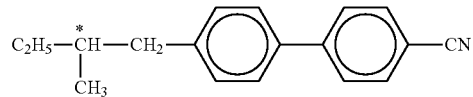
CB 15
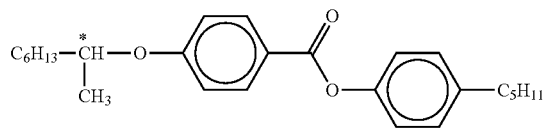
CM 21
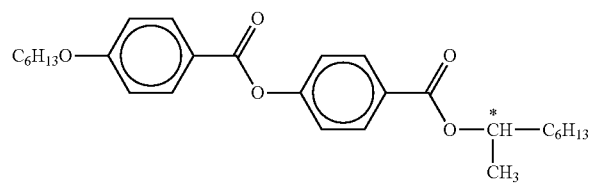
R/S-811

TABLE C-continued
Table C indicate possible dopants which can be added to the LC media according to the invention.
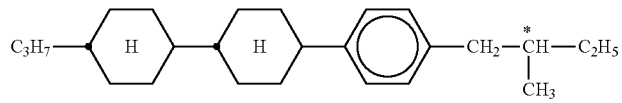
CM 44
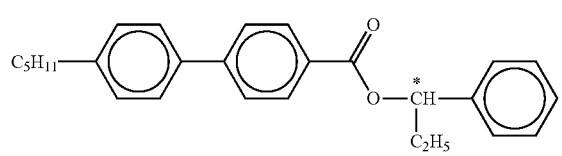
CM 45
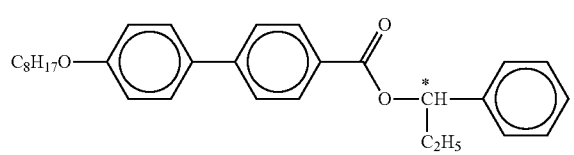
CM 47
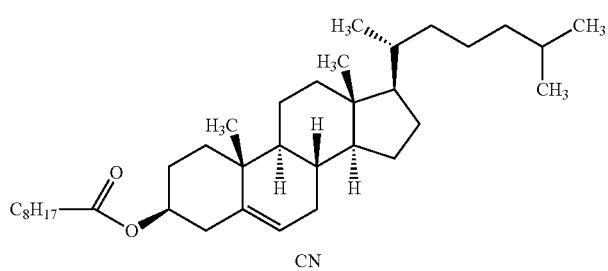
CN
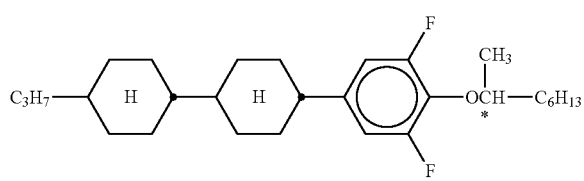
R/S-2011
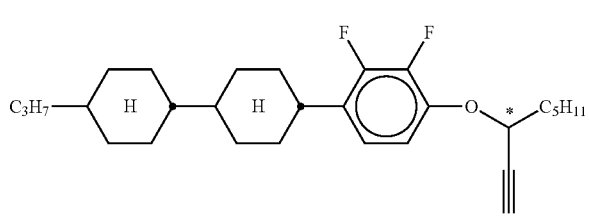
R/S-3011
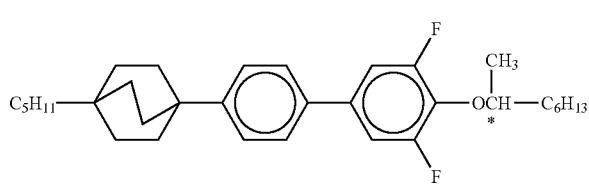
R/S-4011

TABLE C-continued

Table C indicate possible dopants which can be added to the LC media according to the invention.

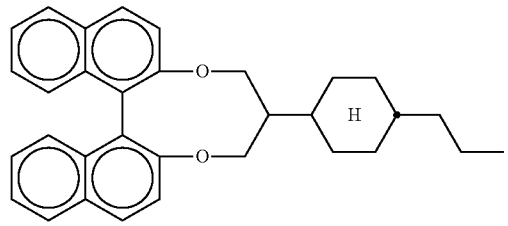

R/S-5011

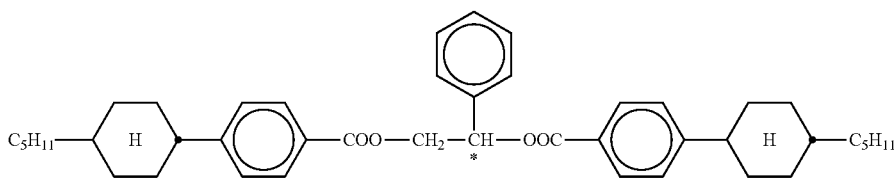

R/S-1011

The LC media preferably comprise 0 to 10% by weight, in particular 0.01 to 5% by weight and particularly preferably 0.1 to 3% by weight, of dopants. The LC media preferably comprise one or more dopants selected from the group consisting of compounds from Table C.

Physical, physicochemical and electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt. The dielectric anisotropy $\Delta \in$ of individual substances is determined at 20° C. and 1 kHz. To this end, 5-10% by weight of the substance to be investigated is measured dissolved in the dielectrically positive mixture ZLI-4792 (Merck KGaA), and the measurement value is extrapolated to a concentration of 100%. The optical anisotropy $\Delta n$ is determined at 20° C. and a wavelength of 589.3 nm, and the rotational viscosity $\gamma_1$ is determined at 20° C., both likewise by linear extrapolation. The clearing point is determined on the pure substance or, if that is not possible, likewise by extrapolation from ZLI-4792.

In addition, the following abbreviations and symbols are used:
$V_0$ threshold voltage, capacitive [V] at 20° C.,
$V_{10}$ optical threshold for 10% relative contrast [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\in_\perp$ dielectric susceptibility perpendicular to the director at 20° C. and 1 kHz,
$\in_\parallel$ dielectric susceptibility parallel to the director at 20° C. and 1 kHz,
$\Delta \in$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN],
LTS low-temperature stability (phase), determined in test cells or on a stock quantity (bulk).

Unless explicitly noted otherwise, all concentrations in the present application are indicated in percent by weight and relate to the corresponding mixture as a whole without solvents.

The term "threshold voltage" for the present invention relates to the capacitive threshold ($V_0$), also called the Freedericks threshold, unless explicitly indicated otherwise. In the examples, as generally usual, the optical threshold for 10% relative contrast ($V_{10}$) may also be indicated.

The test cells used for measurement of the capacitive threshold voltage $V_0$ and for $V_{10}$ are constructed from substrates consisting of soda-lime glass coated with polyimide alignment layers (Durimid 32 with diluent (70% of NMP+ 30% of xylene) in the ratio 1:4) from Arch Chemicals, which are rubbed antiparallel to one another and have a surface tilt of quasi 0 degrees. The area of the transparent, virtually square ITO electrodes is 1 cm². The capacitive threshold voltage is determined using a standard commercial high-resolution LCR meter (for example Hewlett Packard 4284A LCR meter).

The following abbreviations are used:
LC liquid-crystal or liquid-crystalline
THF tetrahydrofuran
MTB ether methyl t-butyl ether

EXAMPLE 1

Step 1.1

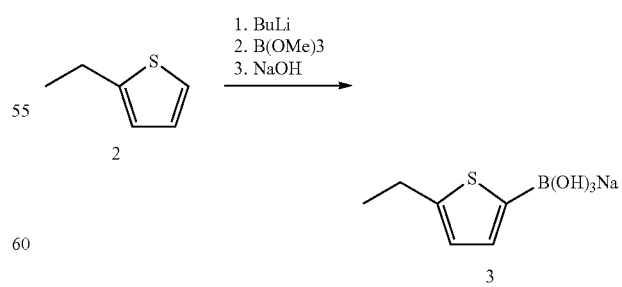

656 ml (15% solution in n-hexane) (1.04 mol) of butyllithium are added to a solution of 116 g (950 mmol) of 2-ethylthiophene in 200 ml of THF at −70° C. under nitrogen. The batch is subsequently stirred at −70° C. for 30 min and at −20° C. for 20 min. 124 ml (1.09 mol) of trimethyl borate are added to the mixture at −70° C., and the mixture is stirred at low temperature for 30 min. The cold bath is removed, and the batch is diluted with 500 ml of water at −15° C. and acidified using hydrochloric acid. The aqueous phase is extracted with MTB ether, and the combined organic phases are washed with sat. sodium chloride solution, dried over sodium sulfate and evaporated. The residue is dissolved in 1000 ml of THF, and 80 ml of 50% sodium hydroxide solution are added with stirring and cooling. The batch is cooled to −10° C., and the precipitated solid is separated off.

Step 1.2

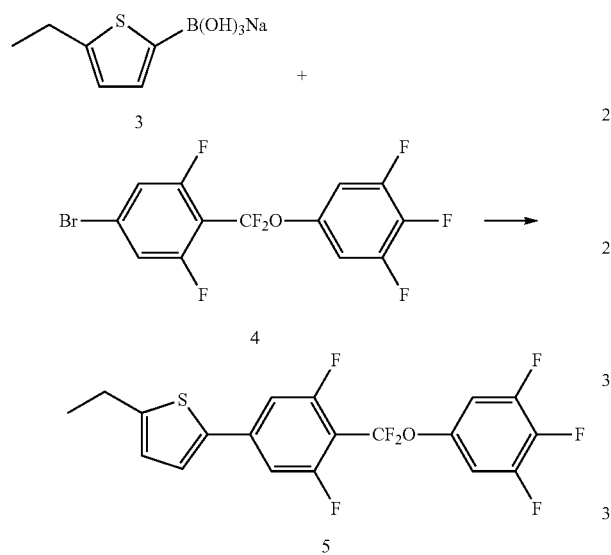

30.9 g (112 mmol) of sodium metaborate octahydrate are initially introduced in 45 ml of water and 125 ml of THF, and 1.1 g (1.5 mmol) of bis-(triphenylphosphine)palladium(II) chloride and 0.1 ml (1.5 mmol) of hydrazinium hydroxide are added. After 5 min, 14.7 g (75 mmol) of the boronate 3 and 29.2 g (75 mmol) of the bromide 4 are added, and the batch is heated at the boil for 8 h. The batch is subsequently diluted with MTB ether. The organic phase is evaporated, and the residue is passed over silica gel (n-heptane). The further purification is carried out by crystallisation from n-pentane (m.p. 36° C.).

C 36 I
$\Delta n = 0.128$
$\Delta \varepsilon = 24$
$\gamma_1 = 47$ mPa·s

The following compounds are prepared analogously:

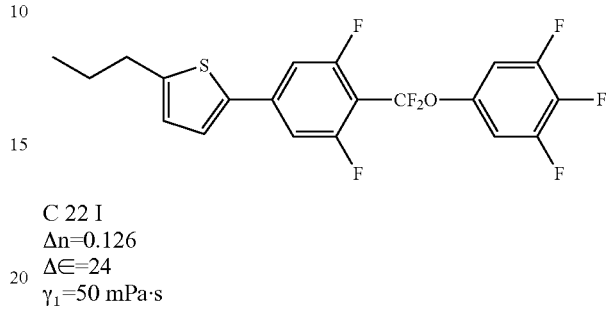

C 22 I
$\Delta n = 0.126$
$\Delta \varepsilon = 24$
$\gamma_1 = 50$ mPa·s

EXAMPLE 2

Step 2.1

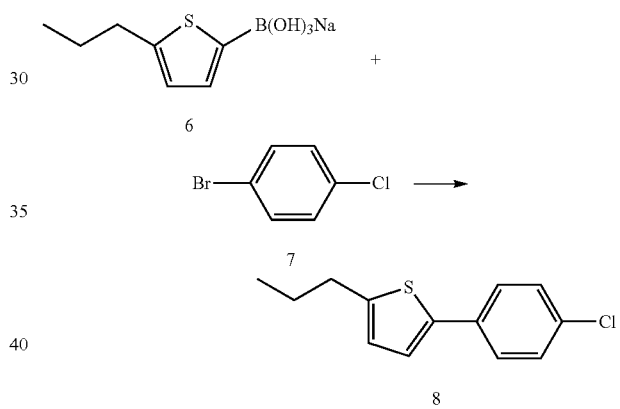

The intermediate 8 is prepared analogously to step 1.2.

Step 2.2

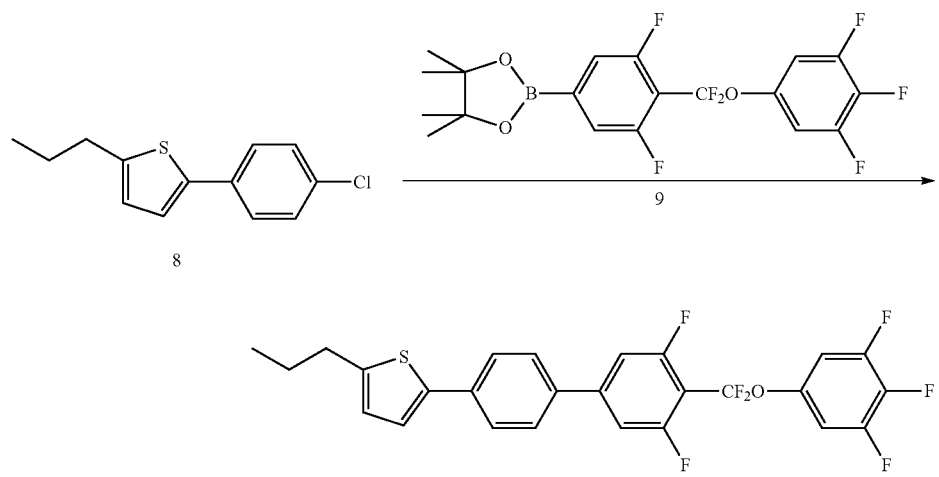

The product 10 is prepared in accordance with the reaction conditions for step 1.2.

C 143 N (138) I

Δn=0.243

Δε=29

The bromine atom on the thiophene derivative 11 can be replaced by a fluorine atom in accordance with *Synth. Commun.* 2008, 38 (1), 72-76 or *Eur. J. Org. Chem.* 2005, 1, 91-97. The boronate is subsequently prepared analogously to the procedure indicated above (step 1.1).

EXAMPLE 3

Step 3.1

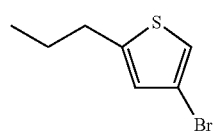

11

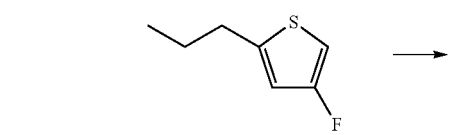

12

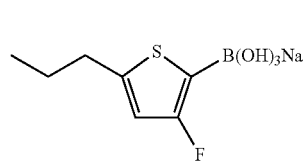

13

Step 3.2

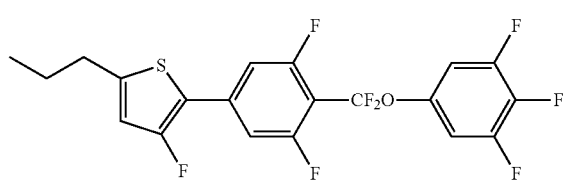

14

Substance 14 is prepared from the boronate of the formula 13 by the method described under Example 1 (step 1.2).

EXAMPLE 4

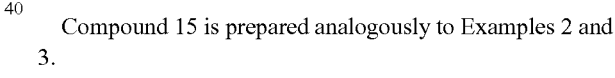

15

Compound 15 is prepared analogously to Examples 2 and 3.

EXAMPLE 5

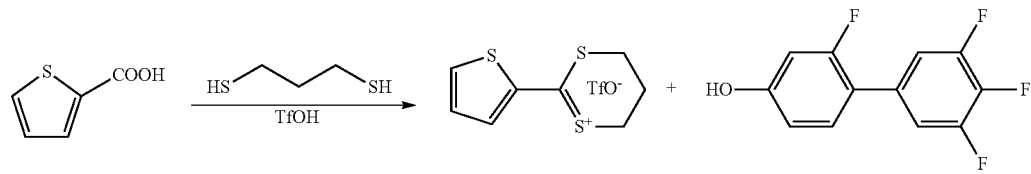

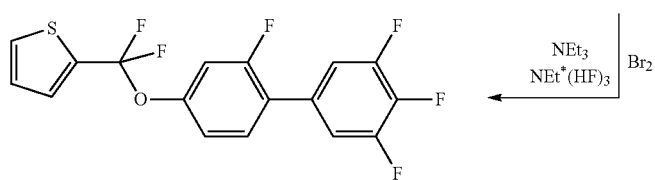

16

Compound 16 can be prepared by the relevant processes from the known precursors indicated (cf. general part).

C 68 I
$\Delta n = 0.098$
$\Delta \varepsilon = 17$
$\gamma_1 = 57$ mPa·s

The following compound is prepared analogously:

17

Mixture Example M1

| The mixture is highly suitable for TN-TFT. | | | |
|---|---|---|---|
| CC-3-V | 32.5% | S → N [° C.]: | <−30.0 |
| CCQU-3-F | 7.0% | Clearing point [° C.]: | +81 |
| SUQU-2-F | 13.0% | Δn [589 nm; 20° C.]: | +0.127 |
| PGU-3-F | 2.0% | Δε | +21.8 |
| CCP-V-1 | 7.5% | $\gamma_1$ [mPa · s; 20° C.]: | 107 |
| APUQU-3-F | 8.0% | | |
| PGUQU-3-F | 5.0% | $V_{10}$ [V]: | 0.97 |
| PGUQU-4-F | 8.0% | $V_{90}$ [V]: | 1.49 |
| PGUQU-5-F | 7.0% | | |
| DPGU-4-F | 10.0% | | |
| | 100.0% | | |

Mixture Example M2

| The mixture is highly suitable for TN-TFT. | | | |
|---|---|---|---|
| CC-3-V | 35.0% | S → N [° C.]: | <−40 |
| SUQU-2-F | 14.0% | Clearing point [° C.]: | 80.5 |
| PGU-3-F | 5.0% | Δn [589 nm; 20° C.]: | 0.126 |
| CCP-V-1 | 16.0% | Δε | +16.5 |
| PGUQU-3-F | 5.0% | $\gamma_1$ [mPa · s; 20° C.]: | 89 |
| PGUQU-4-F | 7.0% | | |
| PGUQU-5-F | 8.0% | $V_{10}$ [V]: | 1.10 |
| DPGU-4-F | 10.0% | $V_{90}$ [V]: | 1.55 |
| | 100.0% | | |

Mixture Example M3

| The mixture is highly suitable for TN-TFT. | | | |
|---|---|---|---|
| CC-3-V | 29.5% | S → N [° C.]: | <−30.0 |
| SUQU-2-F | 15.0% | Clearing point [° C.]: | 78.5 |
| PGU-3-F | 8.5% | Δn [589 nm; 20° C.]: | 0.130 |
| PGP-2-2V | 4.0% | Δε | +18 |
| CCP-V-1 | 14.0% | $\gamma_1$ [mPa · s; 20° C.]: | 95 |
| APUQU-2-F | 9.0% | | |
| APUQU-3-F | 10.0% | $V_{10}$ [V]: | 1.07 |
| PGUQU-3-F | 5.0% | $V_{90}$ [V]: | 1.62 |
| CPGU-3-OT | 5.0% | | |
| | 100.0% | | |

Mixture Example M4

| The mixture is highly suitable for TN-TFT. | | | |
|---|---|---|---|
| CC-3-V | 30.0% | S → N [° C.]: | <−25 |
| SUQU-2-F | 15.0% | Clearing point [° C.]: | 80.5 |
| PGU-3-F | 7.0% | Δn [589 nm; 20° C.]: | 0.129 |
| PGP-2-2V | 5.0% | Δε | +16.3 |
| CCP-V-1 | 15.5% | $\gamma_1$ [mPa · s; 20° C.]: | 92 |
| APUQU-2-F | 8.5% | | |
| APUQU-3-F | 9.0% | $V_{10}$ [V]: | 1.11 |
| PGUQU-3-F | 5.0% | $V_{90}$ [V]: | 1.68 |
| CPGU-3-OT | 5.0% | | |
| | 100.0% | | |

Mixture Example M5

| The mixture is highly suitable for TN-TFT. |  |
|---|---|
| CC-3-V | 35.0% |
| SUQU-2-F | 12.5% |
| CCP-V-1 | 15.0% |
| PGUQU-3-F | 4.0% |
| CPGU-3-OT | 5.0% |
| APUQU-2-F | 3.0% |
| APUQU-3-F | 10.0% |
| PGP-2-2V | 7.5% |
| PGU-3-F | 8.0% |
| | 100.0% |

Mixture Example M6

| The mixture is highly suitable for IPS. | | | |
|---|---|---|---|
| CC-3-V | 40.0% | | |
| CCGU-3-F | 6.0% | Clearing point [° C.]: | 75 |
| PGUQU-3-F | 5.0% | Δn [589 nm; 20° C.]: | 0.103 |
| APUQU-2-F | 3.0% | Δε | +14.3 |
| APUQU-3-F | 11.0% | $\gamma_1$ [mPa · s; 20° C.]: | 79 |
| CPGU-3-OT | 3.0% | | |
| CCQU-3-F | 10.0% | $V_0$ [V]: | 0.92 |
| CCQU-5-F | 7.0% | | |
| PGU-2-F | 5.0% | | |
| SUQU-2-F | 10.0% | | |
| | 100.0% | | |

Mixture Example M7

| The mixture is highly suitable for IPS. | | | |
|---|---|---|---|
| SUQU-2-F | 14.0% | | |
| CCGU-3-F | 3.0% | Clearing point [° C.]: | 88 |
| CC-3-V | 32.0% | Δn [589 nm; 20° C.]: | 0.124 |
| CCP-V-1 | 10.0% | Δε | +11.3 |
| CCP-V2-1 | 11.0% | $\gamma_1$ [mPa · s; 20° C.]: | 86 |
| PGP-2-3 | 5.0% | | |
| PGP-2-4 | 5.0% | $V_0$ [V]: | 1.16 |
| APUQU-2-F | 2.0% | LTS (bulk, −30° C.): | >500 h |
| APUQU-3-F | 11.0% | | |
| PGUQU-3-F | 7.0% | | |
| | 100.0% | | |

Mixture Example M8

| The mixture is highly suitable for TN-TFT. | | | |
|---|---|---|---|
| PGUQU-3-F | 7.5% | | |
| CPGU-3-OT | 3.5% | Clearing point [° C.]: | 74.5 |
| SUQU-2-F | 9.0% | Δn [589 nm; 20° C.]: | 0.131 |
| PP-1-2V1 | 1.5% | Δε | +7.4 |
| CC-3-V | 44.0% | $\gamma_1$ [mPa · s; 20° C.]: | 56 |
| PGP-2-2V | 18.0% | | |
| CPU-3-OXF | 16.5% | $V_{10}$ [V]: | 1.55 |
| | 100.0% | $V_{90}$ [V]: | 2.30 |

Mixture Example M9

| The mixture is highly suitable for TN-TFT. | | | |
|---|---|---|---|
| CC-3-V | 40.5% | | |
| APUQU-2-F | 4.0% | Clearing point [° C.]: | 75 |
| APUQU-3-F | 8.5% | Δn [589 nm; 20° C.]: | 0.126 |
| CPGU-3-OT | 2.0% | Δε | +12.0 |
| PGUQU-3-F | 9.0% | $\gamma_1$ [mPa · s; 20° C.]: | 71 |
| SUQU-3-F | 8.0% | | |
| PGP-2-2V | 9.0% | $V_{10}$ [V]: | 1.21 |
| CPU-3-OXF | 19.0% | $V_{90}$ [V]: | 1.83 |
| | 100.0% | | |

Further combinations of the embodiments and variants of the invention in accordance with the description also arise from the following claims.

The invention claimed is:
1. A compound of formulae I1 to I6:

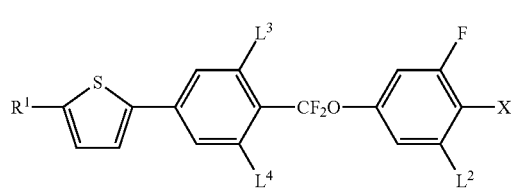

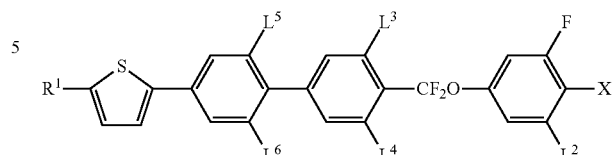

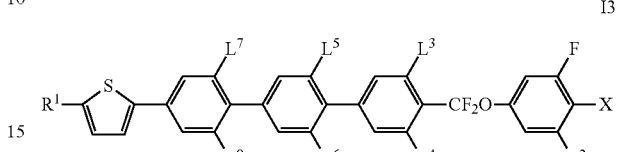

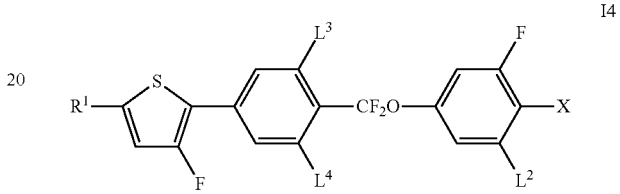

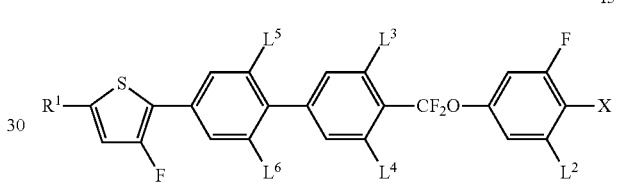

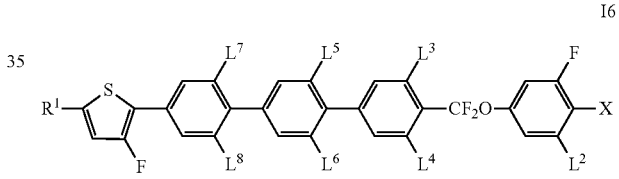

in which
$R^1$ denotes H, a halogenated or unsubstituted alkyl radical having 1 to 15 C atoms, where, in addition, one or more $CH_2$ groups in these radicals are each optionally replaced, independently of one another, by —C≡C—, —CH=CH—, —(CO)O—, —O(CO)—, —(CO)— or —O— in such a way that O atoms are not linked directly to one another, and where $R^2$ can additionally denote F, Cl, Br, CN, SCN, NCS or $SF_5$, X denotes F, $OCF_3$, CN, $CF_3$, SCN, $SF_5$, NCS, Cl, $OCHF_2$, $OCHFCF_3$, or $OCF_2CHFCF_3$, and $L^2$, $L^3$, $L^4$, $L^5$, $L^6$, $L^7$ and $L^8$ independently of one another, denote H or F,

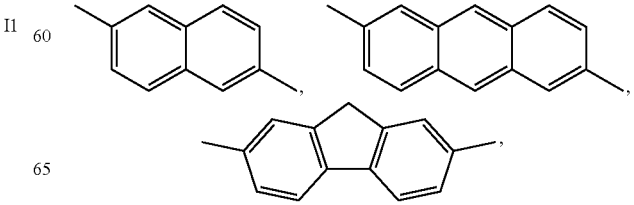

-continued

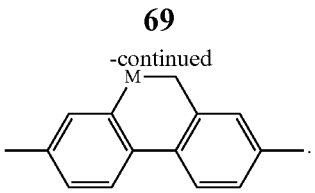

2. A compound according to claim 1, wherein $R^1$ denotes alkyl, alkoxy, alkenyl or alkenyloxy, each having up to 8 carbon atoms.

3. A compound according to claim 1, wherein $L^2$ denotes fluorine.

4. A process for the preparation of compounds according to claim 1, comprising:

reacting a thiophene compound of formula IIa or IIb

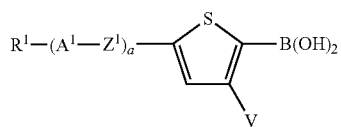 IIa or a corresponding boronate containing the end group —B(OH)$_3^-$ or —B(OH)$_3$M, in which M represents a monovalent ionic radical,

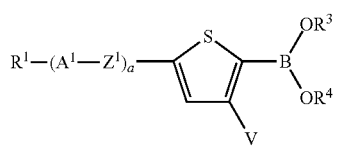 IIb in which
$R^1$, $A^1$, $Z^1$, V and a, in each case independently, are as defined in claim 1, and
$R^3$, $R^4$ denote alkyl having 1-12 C atoms or $R^3+R^4$ together can also denote $C_1$-$C_6$-alkylene, or 1,2-phenylene,
where $R^3$, $R^4$ and $R^3+R^4$ may also be substituted,
with a compound of formula III

 III in which
$Z^2$, $Z^3$, $A^2$, $A^3$, $A^4$, b, c and $R^2$ are as defined in claim 1, and
Hal denotes —O(SO$_2$)CF$_3$, Cl, Br or I,
in the presence of a transition-metal catalyst.

5. A liquid-crystalline medium comprising one or more compounds according to claim 1.

6. A liquid-crystalline medium comprising at least two mesogenic compounds, wherein said medium comprises at least one compound according to claim 1.

7. A liquid-crystalline medium according to claim 6, wherein said medium further comprises one or more compounds of formulae II and/or III:

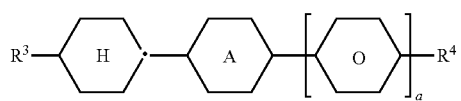 II

 III in which
ring A denotes 1,4-phenylene or trans-1,4-cyclohexylene,
a is 0 or 1,
$R^3$ in each case, independently of one another, denotes alkyl having 1 to 9 C atoms or alkenyl having 2 to 9 C atoms, and
$R^4$ in each case, independently of one another, denotes an unsubstituted or halogenated alkyl radical having 1 to 12 C atoms, where, in addition, one or two non-adjacent CH$_2$ groups are each optionally replaced by —O—, —CH=CH—, —CH=CF—, —(CO)—, —O(CO)— or —(CO)O— in such a way that O atoms are not linked directly to one another.

8. A liquid-crystalline medium according to claim 6, wherein said medium further comprises one or more compounds of formulae X, XI and/or XXVI:

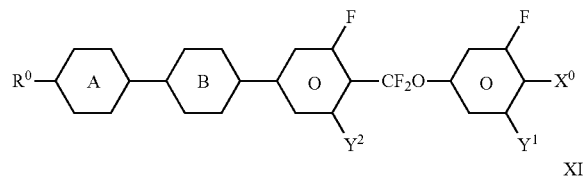 X

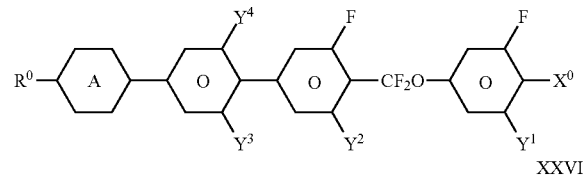 XI

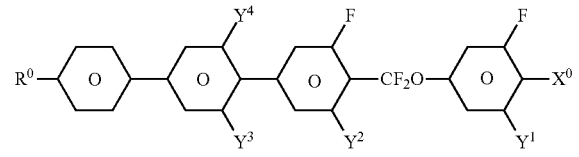 XXVI in which
$R^0$ denotes an alkyl or alkoxy radical having 1 to 15 C atoms, where, in addition, one or more CH$_2$ groups in these radicals are each optionally replaced, independently of one another, by —C≡C—, C—F$_2$O—, —CH=CH—,

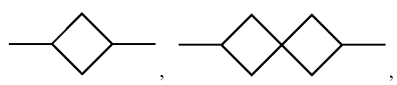

—O—, —(CO)O— or —O(CO)— in such a way that O atoms are not linked directly to one another, and in which, in addition, one or more H atoms are each optionally replaced by halogen,

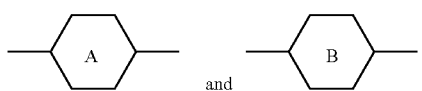

each, independently of one another, denote

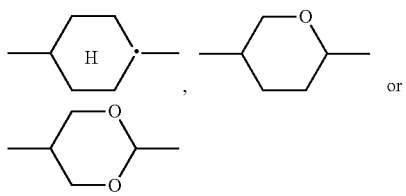

X⁰ denotes F, Cl, CN, SF₅, SCN, NCS, a halogenated alkyl radical having up to 6 C atoms, a halogenated alkenyl radical having up to 6 C atoms, a halogenated alkoxy radical having up to 6 C atoms or a halogenated alkenyloxy radical having up to 6 C atoms, and $Y^1, Y^2, Y^3, Y^4$ each, independently of one another, denote H or F.

9. A liquid-crystalline medium according to claim 6, wherein the total content of CF₂O-bridged compounds, including the compounds of the formula I, is 35% by weight or more.

10. A method comprising employing the liquid-crystalline medium according to claim 6 in an electro-optical process.

11. An electro-optical liquid-crystal display containing a liquid-crystalline medium according to claim 6.

12. A compound according to claim 1, wherein X is F, Cl, CN, CF₃ or OCF₃.

13. A compound according to claim 1, wherein $R^1$ and $R^2$ are not simultaneously H.

14. A compound according to claim 1, wherein at least one of $L^2$, $L^3$ and $L^4$ is F.

15. A compound according to claim 1, wherein at least one of $L^5$ and $L^7$ is H.

16. A compound according to claim 1, wherein said compound is selected from the following compounds:

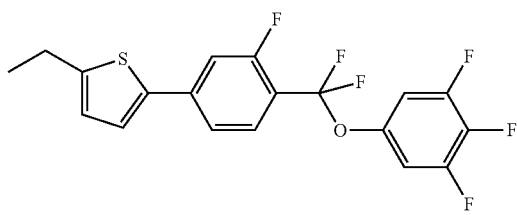

-continued

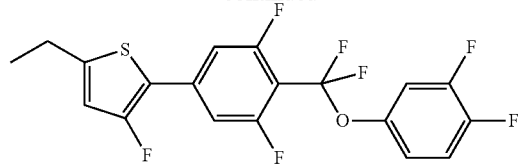

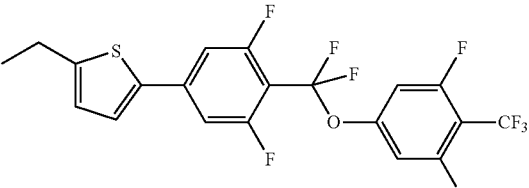

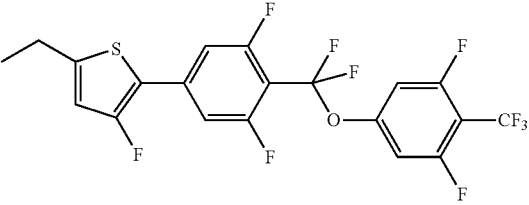

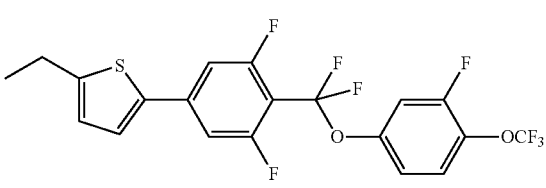

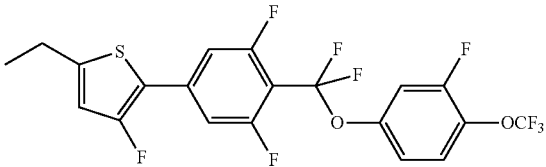

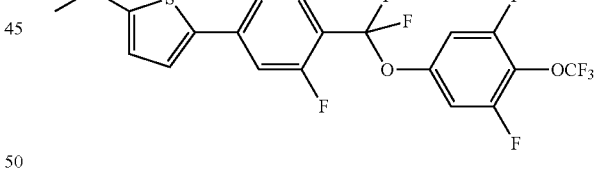

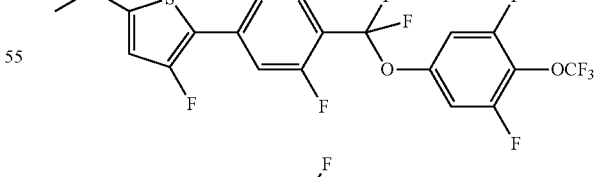

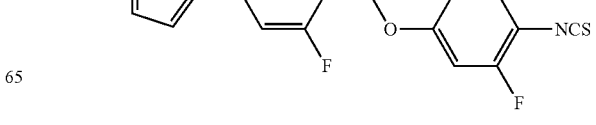

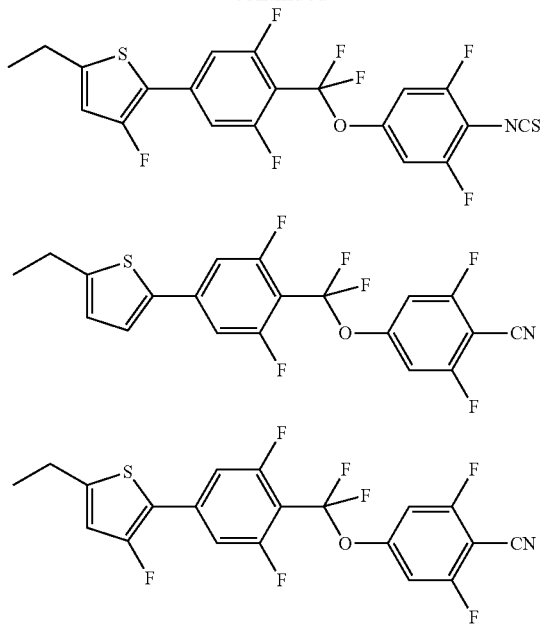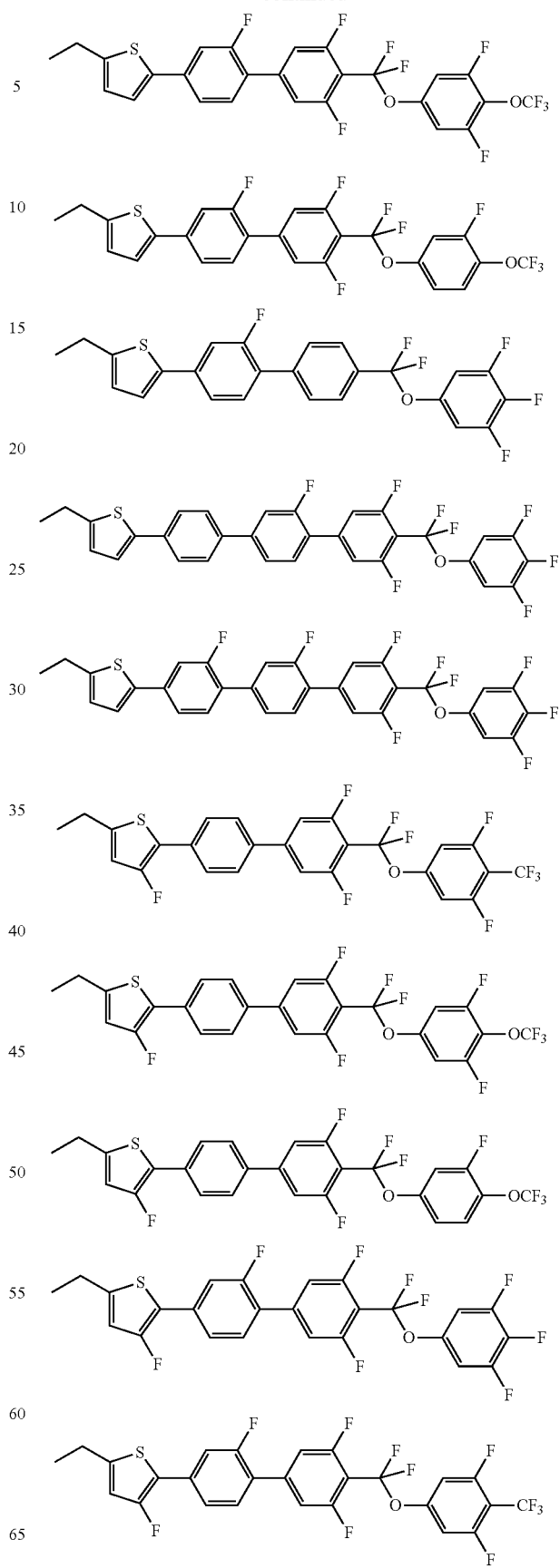

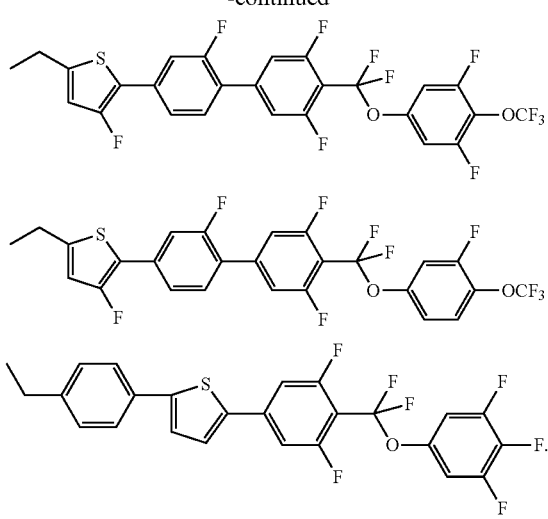

17. A liquid-crystalline medium according to claim 6, wherein said medium further comprises one or more compounds of formulae IIa to IIi and/or one or more compounds of formulae IIIa to IIIb:

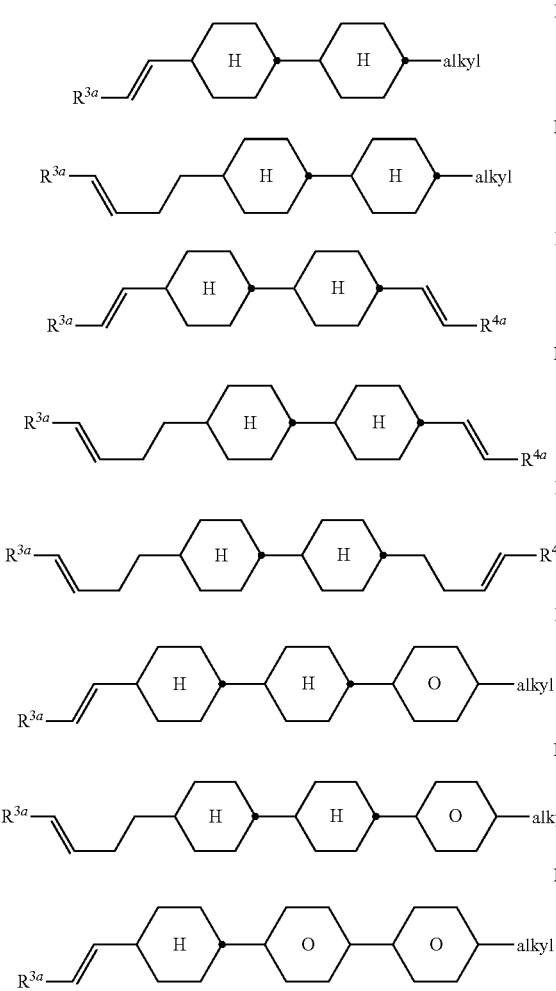

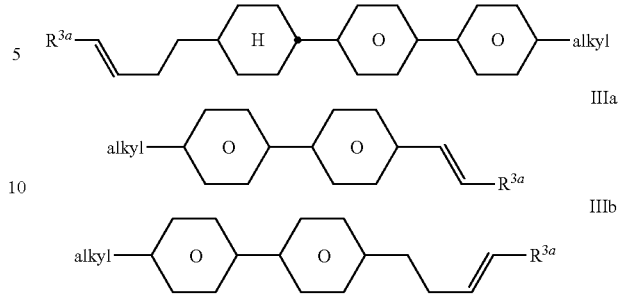

in which $R^{3a}$ and $R^{4a}$ each, independently of one another, denote H, $CH_3$, $C_2H_5$ or $C_3H_7$, and "alkyl" denotes a straight-chain alkyl group having 1 to 8 C atoms.

18. A liquid-crystalline medium according to claim 6, wherein said medium further comprises one or more compounds of formula VI-2:

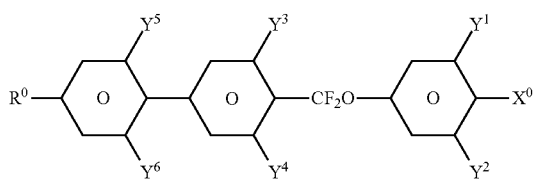

wherein
$R^0$ denotes an alkyl or alkoxy radical having 1 to 15 C atoms, where, in addition, one or more $CH_2$ groups are each optionally replaced, independently of one another, by —$CF_2O$—, —CH=CH—,

[cyclobutane diagrams]

—O—, —(CO)O— or —O(CO)— in such a way that O atoms are not linked directly to one another, and in which, in addition, one or more H atoms may be replaced by halogen,
$X^0$ denotes F, Cl, CN, $SF_5$, SCN, NCS, a halogenated alkyl radical, halogenated alkenyl radical, halogenated alkoxy radical or halogenated alkenyloxy radical, each having up to 6 C atoms, and
$Y^{1-6}$ each, independently of one another, denote H or F.

19. A liquid-crystalline medium according to claim 1, wherein said medium contains 1-25% by weight, of compounds of the formulae I1-I6.

20. A liquid-crystalline medium according to claim 7, wherein said medium contains 25-80% by weight of compounds of the formulae II and/or III.

21. A liquid-crystalline medium according to claim 17, wherein said medium contains 20-70% by weight of compounds of the formula IIa.

22. A liquid-crystalline medium according to claim 18, wherein said medium contains 2-25% by weight of compounds selected from formulae I and VI-2.

23. A liquid-crystalline medium according to claim 8, wherein said medium contains in total 2-30% by weight of compounds of formulae XI and XXVI together.

* * * * *

UNITED STATES PATENT AND TRADEMARK OFFICE
CERTIFICATE OF CORRECTION

PATENT NO. : 8,609,714 B2  Page 1 of 1
APPLICATION NO. : 13/202153
DATED : December 17, 2013
INVENTOR(S) : Lars Lietzau et al.

It is certified that error appears in the above-identified patent and that said Letters Patent is hereby corrected as shown below:

In the Claims

Column 68, Lines 60-65 through Column 69, Line 5: delete the following structures:

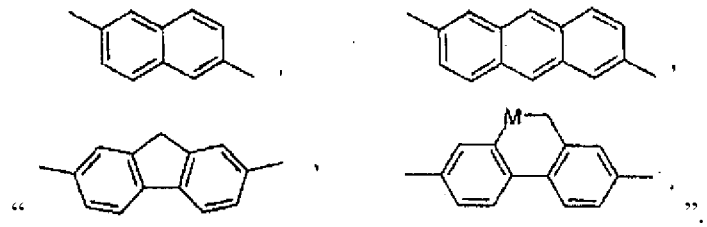

Column 76, Line 37 reads: "by –CF$_2$O-, -CH=CH-," should read -- by -C≡C-, -CF$_2$O-, -CH=CH-, --.

Signed and Sealed this
Twenty-eighth Day of October, 2014

Michelle K. Lee
*Deputy Director of the United States Patent and Trademark Office*